United States Patent [19]

Emini et al.

[11] Patent Number: 5,606,030
[45] Date of Patent: Feb. 25, 1997

[54] COCONJUGATES OF OMPC, HIV RELATED PEPTIDES AND ANIONIC MOIETIES

[75] Inventors: Emilio A. Emini, Paoli, Pa.; William J. Leanza, Berkeley Heights, N.J.; Stephen Marburg, Metuchen, N.J.; Richard L. Tolman, Warren, N.J.

[73] Assignee: Merck & Co., Inc., Rahway, N.J.

[21] Appl. No.: 305,862

[22] Filed: Sep. 14, 1994

Related U.S. Application Data

[63] Continuation of Ser. No. 952,208, Sep. 28, 1992, abandoned, which is a continuation of Ser. No. 715,278, Jun. 19, 1991, abandoned, and Ser. No. 715,276, Jun. 19, 1991, abandoned, which is a continuation-in-part of Ser. No. 555,966, Jul. 19, 1990, abandoned, which is a continuation-in-part of Ser. No. 555,339, Jul. 19, 1990, abandoned.

[51] Int. Cl.$^6$ .................. C07K 17/02; A61K 39/385
[52] U.S. Cl. .................. 530/404; 530/317; 530/324; 530/325; 530/326; 530/327; 530/328; 530/329; 530/330; 530/408; 530/409; 424/188.1; 424/194.1; 424/197.1; 424/208.1
[58] Field of Search .................. 530/324, 330, 530/317, 332, 345, 403–406, 408, 409; 624/188.1, 194.1, 208.1, 197.11

[56] References Cited

U.S. PATENT DOCUMENTS

| | | | |
|---|---|---|---|
| 4,691,006 | 9/1987 | Stevens . | |
| 4,695,624 | 9/1987 | Marburg . | |
| 4,762,913 | 8/1988 | Stevens . | |
| 4,767,842 | 8/1988 | Stevens . | |
| 4,902,506 | 2/1990 | Anderson et al. | 424/92 |
| 4,956,273 | 9/1990 | Kennedy et al. | 435/5 |
| 5,013,548 | 5/1991 | Haynes et al. | 424/89 |
| 5,017,688 | 5/1991 | Gilbert et al. | 530/326 |
| 5,019,387 | 5/1991 | Haynes et al. | 424/89 |

FOREIGN PATENT DOCUMENTS

| | | |
|---|---|---|
| 01611188A3 | 5/1984 | European Pat. Off. . |
| 0186576A2 | 12/1984 | European Pat. Off. . |
| 0311228A2 | 9/1987 | European Pat. Off. . |
| 0311219 | 9/1987 | European Pat. Off. . |
| 0328403A2 | 2/1988 | European Pat. Off. . |
| 0255190A2 | 2/1988 | European Pat. Off. . |
| 0339504A2 | 4/1988 | European Pat. Off. . |
| 0289110 | 11/1988 | European Pat. Off. . |
| 0306219A2 | 3/1989 | European Pat. Off. . |
| 0402088A2 | 6/1989 | European Pat. Off. . |
| 0325270A2 | 7/1989 | European Pat. Off. . |
| 0467701 | 7/1990 | European Pat. Off. . |
| 3802060A1 | 7/1989 | Germany . |
| WO88/00471 | 7/1986 | WIPO . |
| WO88/08429 | 4/1987 | WIPO . |
| 8808429A | 11/1988 | WIPO . |
| WO91/05864 | 10/1989 | WIPO . |
| 91/05864 | 10/1989 | WIPO . |
| WO91/05567 | 10/1989 | WIPO . |
| 90/03984 | 4/1990 | WIPO . |
| 9003984 | 4/1990 | WIPO . |

| | | |
|---|---|---|
| WO92/07876 | 10/1990 | WIPO . |

OTHER PUBLICATIONS

Fauci (1986) PNAS 83:9278–9283.
Rudinger (1976) in J A Parsons ed *Peptide Hormones* pp. 1–7, Univ. Park Press, Baltimore.
Sandstrom et al (1987) Drugs 34:372–390.
Javaherian, et al, PNAS USA 86,6768 (1989).
Marburg, et al., JACS 108, 5282 (1986), Marburg II.
Palker, et al, PNAS USA 85, 1932 (1988), Palker I.
Palker, et al., J. Immunol., 142, 3612 (1989), Palker II.
Blair, et al., J. Imm. Methods, 59: 129–143 (1983).
Devash, et al. PNAS 87: 3445–3449 (1990).
Fauir PNAS 83: 9278–9283 (1986).
Goudsmit, et al., Res. Virol. 140:419–436 (1986).
Rudinger in JA Parsons ed Peptide Hormones, pp. 1–7 University Park Press Baltimore.
Emini, et al., Nature,, vol 20, pp. 728–730 (1992).
Matsushita, et al., J. of Virol., 62, No. 6 pp. 2107–2114 (1988).
Emini et al., J. of Virol., 64, No. 8, pp. 3674–3678 (1990).
Helling, et al., Act Path. Microbiol. Scand. 89, pp. 69–78 (1981).
Girard, et al., Proc. Natl. Acad. Sci. USA, 88, pp. 542–546 (1991).
Biberfeld & Emini, AIDS, 5, (Suppl. 2), pp. S129–S133 (1991).
Goudsmit, et al., P.N.A.S. 85:4478–4482 (1988).
Lowell, et al., Technological Advances in Vaccine Development, pp. 423–432, Alan R. Liss, Inc (1988).
Lowell, et al., J. Exp. Med., 167:658–663 (1988).
Rusche, et al., P.N.A.S. 85:3198–3202 (1988).
Frasch, C. and Robbins, J., J. Exp. Med. 147:629–644 (1978).
Barnes, D., Research News 240, 719–721 (1988).
Hilleman, M., Vaccine 6:175–179 (1988).
Frasch, C. and Gotschlich, E. J. Exp. Med. 140:87–104 (1974).
Putney, S., et al., Chem. Abst. 110:89579f, p. 162 (1988).
Fujii, N., et al., Int. J. Pep. Prot. Res. 26:121–129 (1985).
Robertson, G. et al., J. Virol. Meth. 20:195–202 (1988).

*Primary Examiner*—Kay K. A. Kim
*Attorney, Agent, or Firm*—Joanne M. Giesser; Jack L. Tribble

[57] ABSTRACT

A novel coconjugate comprising an immunogenic protein or protein complex having a first set of covalent linkages to low molecular weight moieties, —a$^-$, which have an anionic or polyanionic character at physiological pH, and a second set of covalent linkages to peptides comprising Human Immunodeficiency Virus (HIV) Principal Neutralizing Determinants (PNDs), or peptides immunologically equivalent therewith, is useful for inducing anti-peptide immune responses in mammals, for inducing HIV-neutralizing antibodies in mammals, for formulating vaccines to prevent HIV infection or disease, including the Acquired Immune Deficiency Syndrome (AIDS), or for treating humans afflicted with HIV infection or disease.

2 Claims, No Drawings

COCONJUGATES OF OMPC, HIV RELATED PEPTIDES AND ANIONIC MOIETIES

This is a continuation of application Ser. No. 07/952,208 filed on Sep. 28, 1992 now abandoned.

Related Applications and claim of priority under 35 U.S.C. §120: which application is a continuation of applications U.S. Ser. No. 715,278, filed Jun. 19, 1991 now abandoned, which was a continuation-in-part of application U.S. Ser. No. 555,339, filed Jun. 19, 1990 now abandoned, and of application U.S. Ser. No. 715,276, filed Jun. 19, 1991 now abandoned, which was a continuation-in-part of application U.S. Ser. No. 555,966, filed Jul. 19, 1990 now abandoned.

BACKGROUND OF THE INVENTION

This invention is concerned with novel covalent peptide-protein conjugates and a method of making and a method of using such conjugates. Principal Neutralizing Determinant (PND) peptides, having the property of binding to antibodies capable of neutralizing Human Immunodeficiency Virus (HIV), are conjugated to a carrier which is comprised of an immunogenic protein or protein complex, preferably the Outer Membrane Protein Complex (OMPC) of Neisseria.

The term "neutralizing" as applied to antibodies means that viral exposure to such antibodies, whether in vitro or in vivo, results in the attenuation or abrogation of any or all of the recognized virus-mediated pathophysiologic functions characteristic of HIV infection and disease including cellular fusion, cellular infection, CD4 receptor bearing cell depletion, and viral proliferation. Neutralizing antibodies meeting these criteria have been detected in the sera of HIV-infected patients and have been induced in animals and humans by immunization with diverse HIV related antigens.

Attenuated or killed whole HIV, HIV subunit proteins, live recombinant vaccinia virus containing incorporated HIV genetic material, and HIV specific peptides have all been evaluated for potential use as protective or therapeutic post-infection immunogens. The whole-virus approach is attended by the danger, however small, of producing an active infection in vaccine recipients, while the subunit-protein-vaccine approach has met with limited success in the induction of virus-neutralizing antibodies. The live-recombinant-vaccinia-virus vaccine approach has promise, but the dangers inherent in the introduction of a live virus, however benign, especially into an already immunocompromised recipient, are obvious. Thus far, peptide based immunogens hold the most promise. The following references provide a general overview of ongoing vaccine evaluations: Lasky, L. A., *Crit. Rev. in Immunol.* 9, 153 (1989); Garrison, L., Clements, L. M., *Comprehensive Therapy* 15, 47 (1989); Dalgleish, A., *Drugs of Today*, 25, 709 (1989); Schulhafer, E. P., Verma, R. S., In Vivo 3, 61 (1989); Fauci, A. S., et al., *Annals of Internal Medicine* 110, 373 (1989); Rosenberg, Z. F., Fauci, A. S., *Advances in Immunol.* 47, 377 (1989); and Snart, R. S. *AIDS* 2, S107 (1988).

Peptides of interest in this invention, hereinafter referred to as Principal Neutralizing Determinants (PNDs), have been identified which are capable of eliciting HIV-neutralizing immune responses in mammals. Although immunogenicity can be conferred on other HIV related or unrelated peptides upon conjugation according to this invention, of particular interest here is the PND located in the HIV IIIB and in most other HIV isolates, such as the MN isolate, at or near the amino acids between 296 and 341 of the HIV envelope glycoprotein, gp120 [numbering according to the scheme of Ratner et al., *Nature* 313, 277 (1985)]. Although the amino acid sequence in this region is variable across HIV isolates, the inter-isolate conserved core amino acid sequence, Gly-Pro-Gly (GPG), appears in over 90% of the isolates tested in one study, while the sequence Gly-Pro-Gly-Arg-Ala-Phe (GPGRAF) appears in a large number of common isolates [Goudsmit, J., Aids 2, S41 (1988)]. Less highly conserved amino acids appear on either side of the GPG trimer. A minimum of between 5 and 8 amino acids, including the GPG, appears to be necessary to induce an HIV neutralizing response [Javaherian et al., *PNAS U.S.A.* 86, 6768 (1989); Goudsmit et al., *Res. Virol.* 140, 419 (1989)].

Linear or cyclic peptides may be utilized to make conjugates which generate HIV neutralizing immune responses. Small divergences in amino acid sequence, for example the substitution of a valine for an alanine, or an aspartate for a glutamate, may in some cases give rise to peptides capable of eliciting similar immune responses. Furthermore, peptides having conserved tertiary structures but having divergent primary structures, as in a series of cyclic PND peptides (cPNDs), may give rise to similar immune responses.

Because HIV is known to be transmitted in either a cell-free or a cell-associated form, it may be an essential requirement that peptidyl epitopes be capable of priming both B-cell- and T-cell- mediated immune responses, such as antibody production and antibody-dependent cellular cytotoxicity, in order to be useful as anti-HIV immunogens. Peptide sequences from the gp120 region described above have been shown to be capable of inducing both types of immune responses [Goudsmit, J., AIDS 2, S41 (1988)].

In addition, in order to generate a useful anti-HIV vaccine, PND peptides, which are generally poorly immunogenic on their own, often must be conjugated to a carrier in a reproducible and quantifiable fashion. Unconjugated peptides are not only poor inducers of B-cell-mediated antibody production, they are also weak inducers of protective T-cell responses. The instant invention overcomes these problems by providing novel immunological conjugates of the PND peptides and immune enhancers.

In U.S. Pat. No. 4,695,624, Marburg et al. disclosed conjugation chemistry for covalently coupling the *Haemophilus influenzae b* capsular polysaccharide, polyribosyl ribitol phosphate (PRP) to the OMPC of *Neisseria meningitidis*. Such conjugates were capable of eliciting anti-PRP immune responses and were useful as immunogens to prevent *Haemophilus influenzae b* infections. The conjugates of this invention raise a completely novel immune response against the HIV PND peptides which are absent in the conjugates of the U.S. Pat. No. 4,695,624.

The novel conjugates of this invention are useful for inducing mammalian immune responses against the peptidyl portion of the conjugate. Where the peptide component of the coconjugate represents an HIV PND peptide, or a peptide capable of eliciting immune responses which recognize HIV PND peptides, the conjugates are useful for inducing anti-HIV PND peptide antibodies in mammals, for inducing HIV-neutralizing antibodies in mammals, or for vaccinating humans prior to or after contraction of HIV infection or disease including AIDS.

SUMMARY OF THE INVENTION

The coconjugates of the invention have the general structure:

or pharmaceutically acceptable salts thereof, wherein:
PEP is an HIV PND peptide, or a peptide capable of raising mammalian immune responses which recognize HIV PNDs;

PRO is an immunogenic protein or protein complex, preferably the outer membrane protein complex (OMPC) of *Neisseria meningitidis b*;

—A— is a covalent linkage, preferably a bigeneric spacer;

—B— is a covalent linkage;

—$a^-$ is a low molecular weight moiety having an anionic or polyanionic character at physiological pH, and comprises from one to five residues of the anionic form of carboxylic, sulfonic, or phosphonic acid;

j is the peptide loading, and is the percentage by mass of peptide in the coconjugate, and is between 1% and 90%, and preferably between 1% and 50% of the total protein mass in the conjugate;

x is the number of moles of —B—$a^-$ in the coconjugate, and is preferably between 1% and 90% of m, and most preferably between 10% and 50% of m; and m is the molar amount of reactive nucleophilic functionalities in the immunogenic protein, PRO, prior to conjugation.

The coconjugate of the invention is prepared by a process that utilizes the available nucleophilic functionalities, "m", found in proteins, such as the amino group of lysine, the imidazole group of histidine, or the hydroxyl groups of serine, threonine, or tyrosine. The process can be carried out in several ways in which the sequence, method of activation, and reaction of protein, peptide, and anionic groups can be varied. The process may comprise the steps of:

Process 1

1a. reacting the protein nucleophilic groups with a reagent, for example with N-acetyl homocysteine thiolactone, which generates thiol groups on the protein, 1b. reacting a fraction of the sulfhydryl groups of the protein -protein from step 1 awith a reagent, such as a maleimidoalkanoic acid, comprising an electrophile and an anion which has a negative charge at physiological pH, 1c. reacting the product of step 1b with peptides previously derivatized so as to append an electrophilic group on the peptide; or Process 2

2a. reacting the protein nucleophilic groups with a bifunctional electrophilic reagent, such as maleimidoalkanoic acid hydroxysuccinimide ester, so as to generate an electrophilic protein, 2b. reacting a fraction of the electrophilic sites on the product of step 2a with a reagent comprising both a nucleophile and an anion, such as α-mercaptoacetic acid, and 2c. reacting the product of step 2b with a peptide containing a nucleophile, such as a thiol group; or Process 3

3a. reacting a fraction of the protein nucleophilic groups with a reagent comprising both an electrophile and an anion or incipient anion, such as N-(bromoacetyl)-6-amino caprole acid, or succinic anhydride, 3b. reacting the residual fraction of nucleophilic groups on the product of step 3a with a reagent, for example with N-acetyl homocysteine thiolactone, which generates thiol groups on the protein, and 3c. reacting the product of step 3b with peptides previously derivatized so as to append an electrophilic group, preferably comprising maleimide, on the peptide; or Process 4

4a. reacting a fraction of the protein nucleophilic groups with a reagent comprising both an electrophile and an anion or incipient anion, such as N-(bromoacetyl)-6-amino caproic acid, or succinic anhydride, 4b. reacting the residual protein nucleophilic groups on the product of step 4a with a bifunctional electrophilic reagent, such as maleimidoalkanoic acid hydroxysuccinimide ester, so as to append electrophilic sites onto the protein, 4c. reacting the product of step 4b with a peptide containing a nucleophilic group, such as a thiol.

Each of these processes appends negative charge and peptides onto an immunogenic protein, and each allows for preparation of a conjugate having different physico-chemical characteristics, such as solubility and propensity to aggregate.

OBJECTS OF THE INVENTION

Accordingly, it is an object of this invention to provide conjugates that are highly immunogenic and are capable of raising an immune response in mammals specific to the epitopes presented by the peptidyl portion of the conjugates. Another object is to provide a covalent coconjugate immunogen wherein the peptide portions of the peptide-protein conjugates are capable of eliciting mammalian immune responses which recognize HIV Principal Neutralizing Determinants. Another object is to provide a coconjugate immunogen capable of raising mammalian antibody responses which neutralize the Human Immunodeficiency Virus. Another object is to provide a process for the high-yield production of covalent peptide-protein conjugates which are soluble in aqueous media. Another object is to provide a method of using such coconjugate immunogens to raise anti-peptide, anti-HIV, or HIV-neutralizing immune responses in mammalian recipients. Another object is to use vaccine formulations containing the coconjugate of this invention to immunize humans prior to or after contraction of HIV infection or disease including AIDS.

DEFINITIONS AND ABBREVIATIONS

| | |
|---|---|
| AA assay | amino acid analysis method wherein peptides or proteins are acid hydrolyzed to the free amino acids and then quantitated |
| | Ac Acetyl |
| Acm | acetamidomethyl thiol protecting group |
| activation | reaction of peptides, proteins, or anionic moieties with a reagent capable of derivatizing the moiety in order to enable subsequent desirable reactions to occur |
| AIDS | Acquired Immune Deficiency Syndrome |
| amino acid | a molecule having both an acid and amino functional group; there are 20 common α-amino acids with the general structure $H_2N$—CHR—COOH, wherein the R group defines the identity of the amino acid; these amino acids may have either a D or L stereochemical form and unless specified otherwise, by the lower-case one letter abbreviation, or by the prefix "D-" before an amino acid name, the amino acid is of the natural or L configuration; the names of the 20 common amino acids and the structure of the R group are identified herein in single-letter code according to the following table: |

| AMINO ACID NAME | 3-letter code | 1-letter code | side-chain (R) |
|---|---|---|---|
| Alanine | Ala | A | —$CH_3$ |

DEFINITIONS AND ABBREVIATIONS

| | | | |
|---|---|---|---|
| Arginine | Arg | R | $-(CH_2)_3NHCHNH_2NH_2^+$ |
| Asparagine | Asn | N | $-CH_2CONH_2$ |
| Aspartic Acid | Asp | D | $-CH_2COOH$ |
| Cysteine | Cys | C | $-CH_2SH$ |
| Glutamic Acid | Glu | E | $-(CH_2)_2COOH$ |
| Glutamine | Gln | Q | $-(CH_2)_2CONH_2$ |
| Glycine | Gly | G | —H |
| Histidine | His | H | $-CH_2$-imidazole |
| Isoleucine | Ile | I | $-CH(CH_3)CH_2CH_3$ |
| Leucine | Leu | L | $-CH_2CH(CH_3)_2$ |
| Lysine | Lys | K | $-(CH_2)_4NH_3^+$ |
| Methionine | Met | M | $-(CH_2)_2SCH_3$ |
| Phenylalanine | Phe | F | $-CH_2$-Phenyl |
| Proline | Pro | P | —α,N-trimethylene |
| Serine | Ser | | $-CH_2OH$ |
| Threonine | Thr | T | $-CH(OH)CH_3$ |
| Tryptophan | Trp | W | $-CH_2$-indole |
| Tyrosine | Tyr | Y | $-CH_2$-phenyl-OH |
| Valine | Val | V | $-CH(CH_3)_2$ |

| | |
|---|---|
| antibody | a protein produced by mamalian B cells that is capable of binding a particular antigen |
| ARC | AIDS-Related Complex |
| AZT | Azidothymidine, an anti-AIDS compound |
| bigeneric spacer | a molecular chain resulting from the reaction of separately derivatized partners; analytical degradation of the coconjugate formed through the spacer allows release and quantitation of the spacer, providing a measure of the degree of covalent attachment |
| BOP | Benzotriazol-l-yloxytris-(dimethylamino)phosphonium hexafluorophosphate |
| capping | the elimination of reactive sites on a coconjugate by reaction with small molecules |
| Cbz | benzyloxycarbonyl |
| conjugate | a complex of discrete chemical entities covalently bound one to the other, wherein at least one entity is a desired antigen (e.g. an HIV PND) and another entity is a carrier |
| coconjugate | a conjugate having a low molecular weight anion covalently coupled to the carrier, in addition to the covalently coupled antigen, this term may be used interchangeably with the abbreviated term, conjugate |
| core amino acids | those amino acids of an HIV PND which are essential for inducing HIV-neutralizing immune responses in a mammal, and comprise a part of the loop amino acids |
| DPPA | diphenylphosphorylazide |
| ELISA | enzyme-linked immunoadsorbant assay |
| fmoc | 9-fluorenylmethoxycarbonyl |
| HIV | Human Immunodeficiency Virus, a member of the lentivirus group and the purported etiologic agent implicated in AIDS and related complexes; HIV is alternatively known as HTLV (Human T-cell Lymphocyte-trophic Virus) III, LAV (Lymphadenopathy Associated Virus), and ARV (AIDS Related Virus) |
| HIV Disease | Clinically recognized disease state characterized by the presence or any of a number of phyorologic dysfunctions known to be associated with HIV infections. |
| immunogen | a molecule useful as a stimulator |

DEFINITIONS AND ABBREVIATIONS

| | |
|---|---|
| | of a mammalian immune response |
| immunologically equivalent peptides | cyclic or linear peptides having in common the function of eliciting HIV neutralizing immune responses in mammals, such as antibodies, which are able to recognize HIV PND epitopes |
| loop amino acids | amino acids comprising the core amino acids in a cyclic HIV PND peptide which go toward formation of the peptide cycle; |
| marker amino acid | an amino acid having a signal in the AA assay which is free of interference by signals generated by other peptide or protein amino acids, for example, norleucine, b-alanine, gamma amino butyric acid, 6-aminohexanoic acid, ornithine |
| Mtr | 4-methoxy-2,3,6-trimethyl phenyl sulfonyl |
| NEM | N-ethylmaleimide |
| OMPC | Outer Membrane Protein Complex of *Neisseria meningitidis*; used as an immunoenhancer and peptide carrier |
| peptide | a polymer of amino acids linked by amide (peptide) bonds |
| PEP | peptide |
| PND | Principal Neutralizing Determinant; the name attributed to peptidyl sequences capable of binding to HIV neutralizing antibodies and capable of raising HIV-neutralizing antibodies in a mammalian recipient upon inoculation with an immunogen containing the PND |
| PnPs | *Streptococcus pneumoniae* capsular polysaccharide; where a number follows the abbreviation, for example PnPs6B, the number indicates the strain of the bacterium |
| PRO | an immunogenic protein |
| protein | a large peptide |
| PRP | Polyribosyl-ribitol phosphate |
| resins | solid support matrices for solid phase peptide synthesis<br>Wang:<br>4-(hydroxymethyl)phenoxymethyl linkage to copolystyrene-1% divinylbenzene resin, which is used for batch Fmoc solid phase peptide synthesis, with final 95% TFA cleavage from the resin and concomitant deprotection of acid sensitive side chain protecting groups;<br>Sasrin:<br>4-(hydroxymethyl)-3-methoxyphenoxy-methyl linkage to copolystyrene-1% divinylbenzene resin, which is used for batch Fmoc solid phase peptide synthesis, with final 1% $TFA/CH_2Cl_2$ cleavage from the resin, leaving intact acid labile side chain protecting groups;<br>Pepsyn KA:<br>4-(hydroxymethyl)phenoxymethyl linkage to polyamide resin adsorbed on to kieselguhr, which is used for continuous flow column Fmoc solid phase peptide |

DEFINITIONS AND ABBREVIATIONS

| | |
|---|---|
| | synthesis. Peptides are cleaved from the resin as described above for Wang resin; |
| Pepsyn KH: | 4-(hydroxymethyl)-3-methoxymethyl linkage to polyamide resin adsorbed on to kieselguhr, which is used for Fmoc solid phase peptide synthesis. Side chain protected peptides are cleaved from the resin as described above for the Sasrin resin |
| S | sulfur |
| SCMHC | S-carboxymethyl homocysteamine, an acid-stable bigeneric spacer released by degradation of covalent coconjugate immunogens and quantifiable by AA assay |
| SCMC | S-carboxymethyl cysteamine, an acid-stable bigeneric spacer released by degradation of covalent coconjugate immunogens and quantifiable by AA assay |
| Z | benzyloxycarbonyl |

DETAILED DESCRIPTION OF THE INVENTION

The novel coconjugate of this invention comprises an immunogenic protein, preferably the outer membrane protein complex (OMPC) of *Neisseria Meningitidis b*, covalently linked to anionic moeities and to HIV PND peptides.

The conjugates are prepared by the process of covalently coupling activated peptide and acidic components to an activated protein. The peptide, protein and acidic components are separately activated to display either pendant electrophilic or nucleophilic groups so that covalent bonds will form between the peptide and the protein and between the acidic component and the protein upon contact.

The covalent coconjugate immunogens that result from the series of reactions described above may conveniently be thought of as a coconjugate in which multiple peptides and multiple acidic functionalities are built upon a foundation of immunogenic protein.

When the peptide components of the coconjugate are capable of eliciting HIV neutralizing immune responses, the conjugates of this invention may be administered to mammals in immunologically effective amounts, with or without additional immunomodulatory, antiviral, or antibacterial compounds, and are useful for inducing mammalian immune responses against the peptidyl portion of the conjugates, for inducing HIV-neutralizing antibodies in mammals, or for making vaccines for administration to humans to prevent contraction of HIV infection or disease including AIDS, or for administration to humans afflicted with HIV infection or disease including AIDS.

The coconjugate of the invention has the general structure:

$$_j(PEP-A-)-PRO-(-B-a^-)_x$$

or pharmaceutically acceptable salts thereof, wherein:

PEP is an HIV PND peptide, or a peptide capable of raising mammalian immune responses which recognize HIV PNDs;

PRO is an immunogenic protein or protein complex, preferably the outer membrane protein complex (OMPC) of *Neisseria meningitidis b*;

—A— is a covalent linkage, preferably a bigeneric spacer;

—B— is a covalent linkage;

—$a^-$ is a low molecular weight moiety having an anionic character at physiological pH, and is preferably from one to five residues of the anionic form of carboxylic, sulfonic, or phosphonic acid;

j is the percentage by mass of peptide in the coconjugate, and is preferably between 1% and 50% of the total protein mass in the conjugate;

x is the number of moles of —B—$a^-$ in the coconjugate, and is preferably between 1% and 90% of m, and most preferably between 10% and 50% of m; and m is the molar amount of reactive nucleophilic functionalities in the immunogenic protein, PRO, prior to conjugation.

The coconjugate of the invention is prepared by a process that utilizes the available nucleophilic functionalities, "m", found in proteins. There are a total of "n" functional groups, $(F)_n$, on any protein, and m is that subset of functionalities which are both available for reaction and have a nucleophilic character, such as the amino group of lysine, the imidazole group of histidine, or the hydroxyl groups of serine, threonine, or tyrosine. In practical terms, the value "m" may be determined by an appropriate assay which may comprise thiolation with N-acetyl homocysteine thiolactone, followed by Ellman Assay [Ellman, G. L., *Arch. Biochem. Biophys.*, 82, 70 (1959)] for determination of total free sulfydryl groups and/or by alkylation with a bromoacetyl amino acid, assayable by amino acid analysis. The value "j" is related to "m" and "x" through the molecular weight of the peptide. Thus, j=(peptide molecular weight)(m–x)/(total coconjugate protein). Thus, "j" is a percentage by mass of total coconjugate protein.

The process can be carried out in several ways in which the sequence, method of activation, and reaction of protein, peptide, and anionic groups can be varied. The process may comprise the steps of:

Process 1

1a. reacting the protein nucleophilic groups with a reagent, for example with N-acetyl homocysteine thiolactone, which generates thiol groups on the protein, 1b. reacting a fraction of the sulfhydryl groups of the protein from step 1a with a reagent, such as maleimidoalkanoic acid, bromoacetic acid, bromoacetyl-6-aminohexanoic acid, iodoacetic acid, or β-propiolactone, comprising an electrophile and an anion which has a negative charge at physiological pH, 1c. reacting the product of step 1b with peptides previously derivatized so as to append an electrophilic group on the peptide. A preferred embodiment of this invention, which may be prepared according to this process, has the structure:

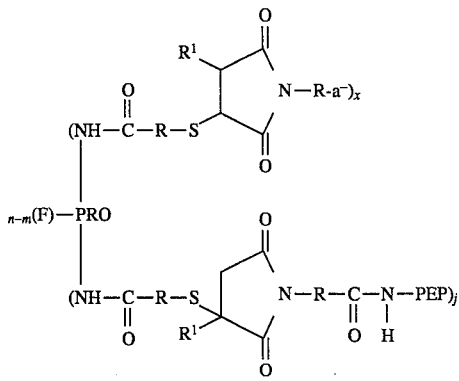

or pharmaceutically acceptable salts thereof
wherein:
PEP, PRO, j, m, and x are as defined supra;
$(F)_{n-m}$ is the total number of functional groups, $F_n$, diminished by the number "m" of functional groups that are derivatized, on PRO;
—R— is:
a) -lower alkyl-,
b) -substituted lower alkyl-,
c) -cycloalkyl-,
d) -substituted cyloalkyl-,
e) -phenyl-;
—$R^1$ is:
a) -hydrogen,
b) -lower alkyl, or
c) —$SO_3H$;
—S— is sulfur; and
—$a^-$ is a low molecular weight anion or a polyanion of up to five residues selected from the anionic form of carboxylic, sulfonic, and phosphonic acids. Lower alkyl includes straight and branched chain alkyls having from one to eight carbon atoms. Substituted lower alkyls and cycloalkyls may have —$NH_2$, —$NHCOCH_3$, alkyl amino, carboxy, carboxy lower alkyl, sulphono, or phosphono substituents.

Likewise, a preferred embodiment of the invention having the structure:

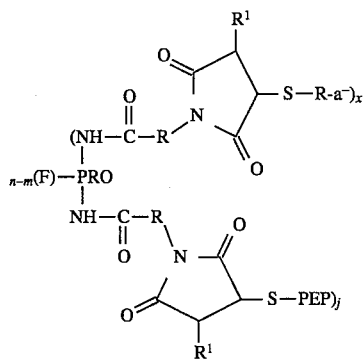

wherein all variables are as defined above, may be prepared by process 2, which comprises the steps of: 2a. reacting the protein nucleophilic groups with a bifunctional electrophilic reagent, such as maleimidoalkanoic acid hydroxysuccinimide ester, so as to generate an electrophilic protein, 2b. reacting a fraction of the electrophilic sites on the product of step 2a with a reagent comprising both a nucleophile and an anion, such as α-mercaptoacetic acid, 2-mercaptoethyl sulfonic acid, 2-mercaptosuccinic acid, 2-mercaptoethyl phosphonic acid, 3-mercapto propionic acid, or 2-mercaptobenzoic acid, and 2c. reacting the product of step 2b with a peptide containing a nucleophile, such as a thiol group.

Similarly, a preferred embodiment of the invention having the structure:

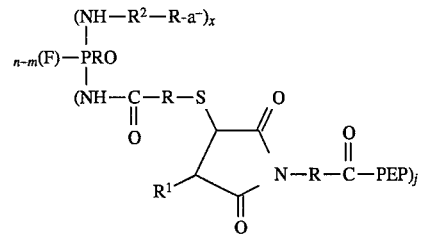

wherein $R^2$ is carbonyl, lower alkyl, or lower alkyl acyl amino and all other variables are as defined above, may be prepared by process 3, which comprises the steps of:

3a. reacting a fraction of the protein nucleophilic groups with a reagent comprising both an electrophile and an anion or incipient anion, such as N-(bromoacetyl)-6-amino caproic acid, glutaric anhydride, tricarballic anhydride, hemimellitic anhydride, pyromellitic anhydride, pthalic anhydride, iodoacetic acid, glyoxylic acid sodium cyanoborohydride, 4-carboxybenzaldehyde-sodium cyanoborohydride, sulfoacetic acid anhydride, or succinic anhydride, 3b. reacting the residual fraction of nucleophilic groups on the product of step 3a with a reagent, for example with N-acetyl homocysteine thiolactone, which generates thiol groups on the protein, and 3c. reacting the product of step 3b with peptides previously derivatized so as to append an electrophilic group, preferably comprising maleimide, on the peptide.

Another preferred embodiment of the coconjugate of this invention having the structure:

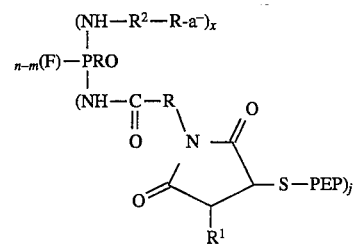

may be prepared by process 4, which comprises the steps of:

4a. reacting a fraction of the protein nucleophilic groups with a reagent comprising both an electrophile and an anion or incipient anion, such as N-(bromoacetyl)-6-amino caproic acid, glutaric anhydride, tricarballic anhydride, hemimellitic anhydride, pyromellitic anhydride, pthalic anhydride, iodoacetic acid, glyoxylic acid-sodiumcyanoborohydride, 4-carboxybenzaldehydesodiumcyanoborohydride, sulfoacetic acid anhydride, or succinic anhydride, 4b. reacting the residual protein nucleophilic groups on the product of step 4a with a bifunctional electrophilic reagent, such as maleimidoalkanoic acid hydroxysuccinimide ester, so as to append electrophilic sites onto the protein, 4c. reacting the product of step 4b with a peptide containing a nucleophilic group, such as a thiol.

Each of the above described processes appends negative charge and peptides onto an immunogenic protein, and each allows for preparation of a conjugate having different physico-chemical characteristics, such as solubility and propensity to aggregate.

A highly preferred embodiment of process 1, is described in detail below and in Scheme A. According to the scheme, the immunogenic protein is the outer membrane protein complex (OMPC) of *Neisseria meningitidis b*, however, other immunogenic proteins may be used. The process comprises the steps of:

a.i. reacting OMPC (I), having a total of "n" moles of nucleophilic groups, including free amino groups, due to the presence of lysines or protein amino-terminii, with a thiolating agent, preferably N-acetyl homocysteine thiolactone, to generate OMPC-SH (II) having "m" moles of sulfhydryl groups available for reaction with a thiophile, and a.ii. quantitating the number of available sulfhydryls appended to OMPC in step 1a.i. to determine the value of "m", preferably by Ellman assay [Ellman, G. L., *Arch. Biochem. Biochem. Biophys.*, 82, 70 (1959)];

b. reacting the product of step a.i. with "x" moles, the concentration of which may be determined, for example, by an Ellman quenching assay, of a thiophile which has an anionic group which does not participate in the thiophilic reaction. Preferably a maleimido-R-acid (maleimido-R—a$^-$), wherein R and —a$^-$ are as defined above, is used. Especially preferred are maleimido ethane phosphonic acid, maleimido ethane sulphonic acid, maleimido-glutaric acid, maleimido-succinic acid, and most preferably maleimido-propionic acid; "x" is between 1% and 90%, and preferably between 10% and 50% of "m" such that "m–x" moles of residual reactive sulfhydryls remain on OMPC (III) after reaction with the thiophile;

c. contacting the product of step b. with an excess, (>m–x), of an HIV PND which has been previously derivatized so as to append an electrophilic group, preferably with a maleimido-alkanoic acid, and most preferably with maleimidopropionic acid (this derivatization is achieved by N-protecting all amino groups on the peptide that should not be derivatized, and reacting the free peptide amino groups with a bifunctional reagent, preferably maleimidoalkanoyloxysuccinimide, and most preferably maleimidopropionyloxysuccinimide), to generate the coconjugate of this invention (IV).

The coconjugate product may be purified by a number of means which take advantage of the unique physico-chemical properties of the coconjugate of the invention. For example, the coconjugate may be purified by dialysis in a buffer having an ionic strength between 0.001M and 1M and a pH between 4 and 11, and most preferably in an aqueous medium having an ionic strength of between 0.01 and 0.1M and a pH of between 6 and 10. Alternatively, or in addition, the coconjugate may be purified by concentrating the coconjugate by ultracentrifugation and discarding the supernatant. The coconjugate may be resuspended in a physiologically acceptable buffer and, optionally, sterile filtered.

SCHEME A
A. THIOLATED OMPC

I. OMPC—(F)$_n$

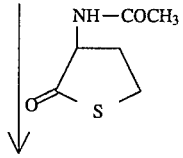

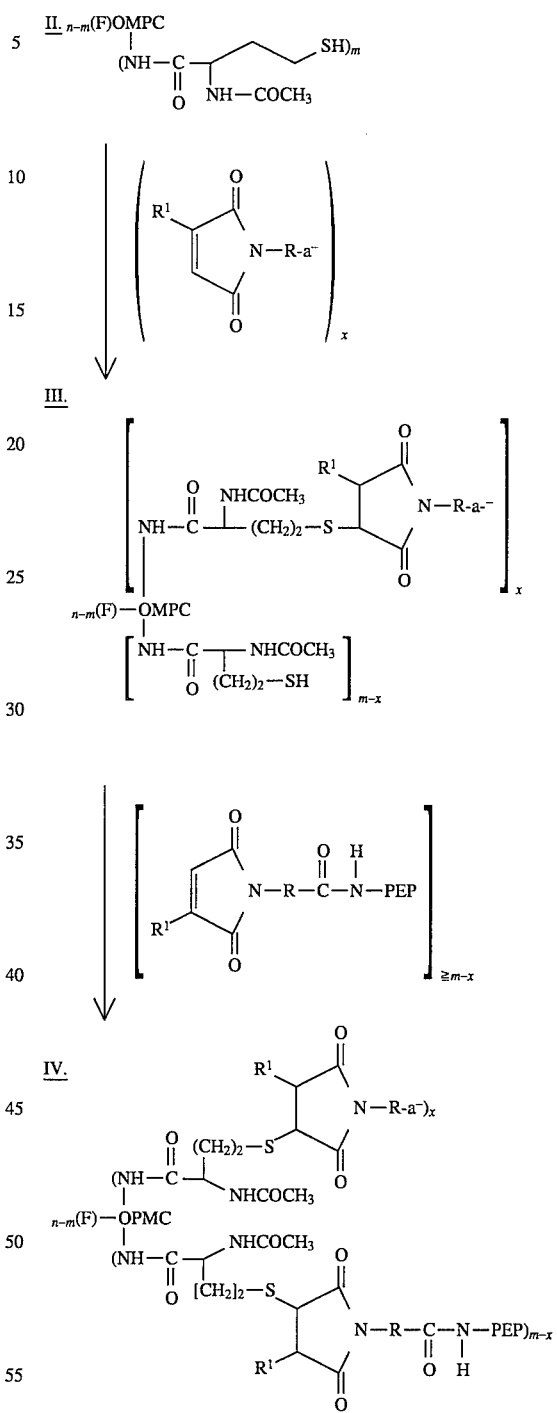

A preferred ratio of "x" to "m" is determined by preparing conjugates with progressively lower amounts (i.e. diminishing values of "x") of the anion, until precipitation of the conjugate occurs.

The process described above and depicted in Scheme A may be modified so that an immunogenic protein is derivatized so as to be covalently linked to a thiophile, such as a derivative of maleimide, while the peptide and low molecular weight anion, —a$^-$ are activated so as to be covalently linked to free sulfhydryls. This and other alternate processes, including those described above as processes 3 and 4, naturally fall within the scope of this disclosure, including variations on these processes, such as variations of sequence of reaction of activated species, or ratios of reactants.

The process for making the conjugates of this invention may be applied to making any coconjugate wherein a peptide-protein conjugate is desired and is particularly significant where enhanced immunogenicity of the peptide is required. Furthermore, the process is especially useful when solubility of a peptide-protein conjugate in aqueous media is normally very low. Absent the unique process herein disclosed, conjugates of HIV PND peptides and OMPC are very poorly soluble in aqueous media, resulting in low product yield, inability to sterile filter the product, and difficulty in handling during the conjugation process itself.

The coconjugates herein described may be included in compositions containing an inert carrier and are useful when appropriately formulated as a vaccine. This may include prior adsorption onto alum or combination with emulsifiers or adjuvants known in the art of vaccine formulation. Methods of using the covalent coconjugate immunogens of this invention include: (a) use as a laboratory tool to characterize HIV PND peptide structure-function relationships; (b) use as an immunogen to raise HIV-neutralizing antibodies in a mammal which antibodies may be isolated and administered to a human so as to prevent infection by HIV, or to limit HIV proliferation post-infection, or to treat humans afflicted by HIV infection or disease including AIDS. (c) use as a vaccine to immunize humans against infection by HIV or to treat humans post-infection, or to boost an HIV-neutralizing immune response in a human afflicted with HIV infection or disease including AIDs.

As a laboratory tool, the coconjugate is useful when administered to a mammal in an immunologically effective amount, to generate anti-PND peptide, anti-HIV, or HIV-neutralizing immune responses. The mammal may be boosted with additional coconjugate to elevate the immune response. Antiserum is obtained from such a mammal by bleeding the mammal, centrifuging the blood to separate the cellular component from the serum, and isolating antibody proteins from the serum if necessary, according to methods known in the art. Such antiserum or antibody preparations may be used to characterize the efficacy of an HIV PND peptide in conjugate in raising mammalian anti-PND peptide, anti-HIV, or HIV-neutralizing antibodies in a mammal. ELISA assays using the unconjugated peptide and the antiserum are useful in vitro assays for measuring the elicitation of anti-peptide antibodies. An in vitro assay for measuring the HIV-neutralizing ability of antiserum comprises incubating a preparation of live HIV with a preparation of the antiserum, then incubating the antiserum-treated HIV preparation with CD4 receptor bearing cells, and measuring the extent of cellular protection afforded by the antiserum. These assays and the characteristics of antiserum produced by a given coconjugate may be used to study the PND peptide structure-function relationship.

The coconjugate is useful for inducing mammalian antibody responses as described in the previous paragraph, and such antibodies may be used to passively immunize humans to prevent HIV infection, or to limit HIV proliferation post-infection, or to treat humans afflicted with HIV infection or disease including AIDS.

The coconjugate is useful as a vaccine which may be administered to humans to prevent HIV infection or proliferation, or to humans suffering from HIV disease of HIV infection, including AIDS and related complexes, or to humans testing seropositive for the HIV virus. The coconjugate may be administered in conjunction with other anti-HIV compounds, such as AZT, or more general anti-viral compounds, or in conjunction with other vaccines, antibiotics, or immunomodulators (see Table I below).

The form of the immunogen within the vaccine takes various molecular configurations. A single molecular species of the antigenic coconjugate IV will often suffice as a useful and suitable antigen for the prevention or treatment of HIV disease including AIDS or ARC. Other antigens in the form of cocktails are also advantageous, and consist of a mixture of conjugates that differ by, for example, the mass ratio of peptide to total protein. In addition, the conjugates in a mixture may differ in the amino acid sequence of the PND.

An immunological vector, carrier or adjuvant may be added as an immunological vehicle according to conventional immunological testing or practice.

Adjuvants may or may not be added during the preparation of the vaccines of this invention. Alum is the typical and preferred adjuvant in human vaccines, especially in the form of a thixotropic, viscous, and homogeneous aluminum hydroxide gel. For example, one embodiment of the present invention is the prophylactic vaccination of patients with a suspension of alum adjuvant as vehicle and a cocktail of conjugates as the selected set of immunogens or antigens.

The vaccines of this invention may be effectively administered, whether at periods of pre-exposure or post-exposure, in combination with effective amounts of the AIDS antivirals, immunomodulators, antibiotics, or vaccines of Table I [source: *Market Letter*, Nov. 30, 1987, p. 26–27; *Genetic Engineering News*, Jan. 1988, Vol. 8, p. 23.]

TABLE I[1]

| A. Antivirals | | |
|---|---|---|
| Drug Name | Manufacturer | Indication |
| AL-721 | Ethigen | ARC, PGL |
| BETASERON (interferon beta) | Triton Biosciences | AIDS, ARC, KS |
| CARRISYN (polymannoacetate) | Carrington Labs | ARC |
| CYTOVENE (ganciclovir) | Syntex | cmv |
| DDC (dideoxycytidine) | Hoffmann-La Roche | AIDS, ARC |
| FOSCARNET (trisodium phosphonoformate) | Astra AB | HIV inf, CMV retinitis |
| HPA-23 | Rhone-Poulenc Sante | HIV infection |
| ORNIDYL (eflornithine) | Merrell Dow | PCP |
| PEPTIDE T (octapeptide sequence) | Peninsula Labs | AIDS |
| RETICULOSE (nucleophospho-protein) | Advanced Viral Research | AIDS, ARC |
| IR (zidovudine; AZT) | Burroughs Wellcome | AIDS, advanced ARC pediatric AIDS, KS, asympt HIV, less severe neurological HIV, in-volvement. |
| RIFABUTIN (ansamycin LM 427) | Adria Labs | ARC |
| (trimetrexate) | Warner-Lambert | PCP |
| UA001 | Ueno Fine Chem Industry | AIDS, ARC |
| VIRAZOLE (ribavirin) | Viratek/ICN | AIDS, ARC, KS |
| WELLFERON (alfa interferon) | Burroughs Wellcome | KS, HIV, in comb with RETROVIR |

TABLE I[1]-continued

| | | |
|---|---|---|
| ZOVIRAX (acyclovir) | Burroughs Wellcome | AIDS, ARC, in comb with RETROVIR |
| B. Immunomodulators | | |
| ABPP (bropirimine) | Upjohn | Advanced AIDS, KS |
| AMPLIGEN (mismatched RNA) (Anti-human alpha interferon antibody) | DuPont HEM Research Advanced Biotherapy Concepts | ARC, PGL AIDS, ARC, KS |
| Colony Stimulating Factor (GM-CSF) | Sandoz Genetics Institute | AIDS, ARC, HIV, KS |
| CL246,738 (CL246,738) | American Cynamid | AIDS |
| IMREG-1 | Imreg | AIDS, ARC, PGL, KS |
| IMREG-2 | Imreg | AIDS, ARC, PGL, KS |
| IMUTHIOL (diethyl dithio carbamate) | Merieux Institute | AIDS, ARC |
| IL-2 (interleukin-2) | Cetus | AIDS, KS |
| IL-2 (interleukin-2) | Hoffmann-La Roche Immunex | AIDS, KS |
| INTRON-A (interferon alfa) | Schering-Plough | KS |
| ISOPRINOSINE (inosine pranobex) | Newport Pharmaceuticals | ARC, PGL, HIV seropositive patients |
| (methionine enkephalin) | TNI Pharmaceuticals | AIDS, ARC |
| MTP-PE (muramyl-tripeptide) | Ciba-Geigy | KS |
| THYMOPENTIN (TP-5) (thymic compound) | Ortho Pharmaceuticals | HIV infection |
| ROFERON (interferon alfa) | Hoffmann-La Roche | KS |
| (recombinant erythropoietin) | Ortho Pharmaceuticals | severe anemia assoc with AIDS & RETROVIR therapy |
| TREXAN (naltrexone) | DuPont | AIDS, ARC |
| TNF (tumor combination necrosis factor) | Genentech | ARC, in interferon gamma |
| C. Antibiotics | | |
| PENTAM 300 (pentamidine isethionate) | LyphoMed | PCP |
| D. Vaccines | | |
| Gag | Merck | AIDS,ARC |

[1]Abbreviations: AIDS (Acquired Immune Deficiency Syndrome); ARC (AIDS related complex); CMV (Cytomegalo-virus, which causes an opportunistic infection resulting in blindness or death in AIDS patients); HIV (Human Immunodeficiency Virus, previously known as LAV, HTLV-III or ARV); KS (Kaposi's sarcoma); PCP (*Pneumonocystis carinii* pneumonia, an opportunistic infection); PGL (persistent generalized lymphadenopathy).

It will be understood that the scope of combinations of the vaccines of this invention with AIDS antivirals, immunomodulators, antibiotics or vaccines is not limited to the list in the above Table, but includes in principle any combination with any pharmaceutical composition useful for the treatment of AIDS. The AIDS or HIV vaccines of this invention include vaccines to be used pre- or post-exposure to prevent or treat HIV infection or disease, and are capable of producing an immune response specific for the immunogen.

The conjugates of this invention, when used as a vaccine, are to be administered in immunologically effective amounts. Dosages of between 1 μg and 500 μg of coconjugate protein, and preferably between 50 μg and 300 μg of coconjugate protein are to be administered to a mammal to induce anti-peptide, anti-HIV, or HIV-neutralizing immune responses. About two weeks after the initial administration, a booster dose may be administered, and then again whenever serum antibody titers diminish. The coconjugate should be administered intramuscularly or by any other convenient or efficacious route, at a concentration of between 10 μg/ml and 1 mg/ml, and preferably between 50 and 500 μg/ml, in a volume sufficient to make up the total required for immunological efficacy. The coconjugate may be preadsorbed to aluminum hydroxide gel or to the Ribi adjuvant (GB 2220211A, US priority document 212,919 filed 29 Jun. 1988, now abandoned) and suspended in a sterile physiological saline solution prior to injection.

The protein moiety should behave as an immune enhancer. It is desirable, in the choice of protein, to avoid those that result in non-specific activation of the recipient's immune response (reactogenicity). In U.S. Pat. No. 4,695,624, Marburg et al. used the outer membrane protein complex (OMPC) derived from *Neisseria meningitidis* to prepare polysaccharide-protein conjugates. OMPC has proven suitable in this invention, though other immunogenic proteins may be used.

Various methods of purifying OMPC from the gram-negative bacteria have been devised [Frasch et al., *J. Exp. Med.* 140, 87 (1974); Frasch et al., J. Exp. Med. 147, 629 (1978); Zollinger et al., U.S. Pat. No. 4,707,543 (1987); Helting et al., Acta Path. Microbiol. Scand. Sect. C. 89, 69 (1981); Helting et al., U.S. Pat. No. 4,271,147]. OMPC used herein was prepared essentially according to the Helting process.

In addition, subunits of OMPC, such as the class 2 protein of *Neisseria meningitidis*, which is the major outer membrane protein [Murakami, K., et al., *Infection and Immunity*, 57, 2318 (1989)], provide immune enhancement necessary to induce mammalian immune responses to HIV PND peptides. These subunits may be derived by dissociation of the isolated OMPC, or alternatively, produced through recombinant expression of the desired immunogenic portions of OMPC. Methods of preparing and using an OMPC subunit are disclosed in co-filed U.S. application Ser. Nos. 555,329; 555,978; and 555,204, all of which are now abandoned, (Merck Case #'s 18159, 18110, and 18160 respectively).

The HIV PND peptides that may be used for making species of the coconjugate of this invention may be linear or cyclic peptides. The linear peptides may be prepared by known solid phase peptide synthetic chemistry, by recombinant expression of DNA encoding desirable peptide sequences, or by fragmentation of isolated HIV proteins. Cyclic HIV PND peptides may be prepared by cyclization of linear peptides, for example (a) by oxidizing peptides containing at least two cysteines to generate disulfide bonded cycles; (b) by forming an amide bonded cycle; (c) by forming a thioether bonded cycle. Processes for making such peptides are described herein but this description should not be construed as being exhaustive or limiting. The conjugates of this invention are useful whenever a component peptide is an HIV PND or is capable of priming mammalian immune responses which recognize HIV PNDs.

PND peptides, both those known in the art and novel compounds disclosed herein and separately claimed in co-filed U.S. application Ser. Nos. 555,112, now abandoned, and 555,227, (Merck Case Nos. 18149, and 18150) are defined as peptidyl sequences capable of inducing an HIV-neutralizing immune response in a mammal, including the production of HIV-neutralizing antibodies.

A major problem overcome by the instant invention is the HIV interisolate sequence variability. The PND identified above occurs in the third hypervariable region of gp120, and although certain amino acids have been found to occur at given locations in a great many isolates, no strictly preserved primary sequence motif exists. This difficulty is surmounted by this invention because it allows conjugation of a cocktail of peptides having PND sequences from as many different HIV isolates as necessary to attain broad protection. Alternatively, a broadly protective cocktail of conjugates may be prepared by mixing conjugates, each of which is prepared separately with a peptide moiety providing protection against a single or several HIV isolates.

The amino acids found near or between amino acids 296 and 341 of gp120 have been shown to meet the criteria which define a PND. In the IIIB isolate of HIV, a 41-amino-acid sequence has been reported as follows (see ABBREVIATIONS AND DEFINITIONS for 3 letter codes and amino acid names): -INCTRPNNNTRKSerIRIQRGPGRAFVTIGKIGNMRQAHCNISer-, with the two cysteines being disulfide bonded to each other to form a loop. The trimer -GPG- is exposed at the PND loop tip. Peptides from different HIV isolates from this same region of gp120 raise isolate-specific neutralizing antibodies when presented to goat and guinea pig immune systems as conjugates with keyhole-limpet hemocyanin. The major neutralizing epitope within the 41-mer sequence, presented above, is comprised by the eight amino acids surrounding and including the -GPG- trimer [Javaherian et al., *PNAS U.S.A.* 86, 6768 (1989)]. In Table II below a number of linear peptides of different length and composition that can be used to prepare the conjugates of this invention are presented. The name of the isolate containing a peptide having the sequence of the tabulated peptide is given, along with a name herein ascribed to that peptide for ease of reference. The letter r- on the left hand side of each peptide represents the possibility of linking the peptide to an immunogenic protein, such as the OMPC at that position. In addition, marker amino acids, such as norleucine and ornithine may form part of r-.

TABLE II

LINEAR HIV PND PEPTIDES

| HIV Isolate | Peptide Sequence | Name |
|---|---|---|
| MN | r-YNKRKRIHIGPGRAFYTTKNIIGT | PND142 |
| SC | r-NNTTRSerIHIGPGRAFYATGDIIGDI | PND-SC |
| IIIB | r-NNTRKSerIRIQRGPGRAFVTIGKIGN | PND135 |
| IIIB | r-RIQRGPGRAFVTIGKIGN | PND135-18 |
| IIIB | r-RIQRGPGRAFVT | PND135-12 |
| MN | r-HIGPGRAF | PND-MN8 |
| MN | r-GPGRAF | PND-MN6 |
| LAV-1 | r-IQRGPGRAF | PND-LAV-1 |
| SF2 | r-IYIGPGRAF | PND-SF2 |
| NY5 | r-IAIGPGRTL | PND-NY5 |
| CDC4 | r-VTLGPGRVW | PND-CDC4 |
| RF | r-ITKGPGRVI | PND-RF |
| ELI | r-TPIGLGQSerL | PND-ELI |
| Z6 | r-TPIGLGQAL | PND-Z6 |
| MAL | r-IHFGPGQAL | PND-MAL |
| Z3 | r-IRIGPGKVF | PND-Z3 |

This list is not an exhaustive list of possible PND sequences. Rather, it is provided as suggestive and illustrative guide as to useful PND primary sequences. Therefore, peptides conjugated as herein described to form the immunogen of this invention are any of the tabulated peptides or immunologically-equivalent variants on the theme suggested by these peptidyl sequences. The nature of the variations is considered next.

The primary sequence of this HIV PND appears to have a conserved core amino acid sequence, comprised by the tetramer sequence -GlyProGlyArg- (-GPGR-), with increasing divergence on either side of this sequence among HIV isolates. Some isolates have sequences that diverge even within the tetramer, having -GPGK-, -GPGQ-, and even -GLGQ- core sequences. All of these possible sequences come within the scope of this disclosure as being peptide sequences that are advantageous for conjugation according to this invention.

The length of the peptide is a significant factor in promoting cross reactive immune responses. That is, an immune response raised against a given peptidyl epitope may recognize similar epitopes from the same or different HIV isolate based on the number of amino acids in the epitope over and above the critical neutralizing epitope. In addition, the length of the peptide is also responsible for determining the probability of exposure to the immune system of the determinant responsible for generating an HIV-neutralizing response.

In order to maximize the probability of relevant epitope presentation, chemistry was developed whereby the PND peptides may be locked into a given three-dimensional configuration. It is known that the 41-amino-acid PND of the HIV IIIB isolate, represented above, is configured as a loop by the presence of the cysteine-to-cysteine disulfide bond. Disulfides, however, are labile and therefore may allow the loop to open and the peptide to exist in a linear form. Therefore, in addition to linear peptides and disulfide-bonded cyclic peptides, novel HIV PND peptides having nonlabile cyclic structures disclosed herein but separately claimed as free peptides in concurrently filed U.S. application Ser. Nos. 555,112, now abandoned, and 555,227, now abandoned, may all be utilized as the PEP component in the formation of the conjugates of this invention.

The peptides that may be used in formation of these conjugates may be derived as fragments of natural proteins (gp120 for example), by recombinant expression of portions thereof, or by chemical synthesis according to known methods in the art. In addition, novel cyclic PNDs may be prepared synthetically according to the processes herein described. The sequences may contain both natural L-amino acids, or unusual or D-amino acids. In addition, the conjugation chemistry is sufficiently flexible so that the appropriate choice of peptide derivatization reagents allows for successful conjugation.

Synthetic peptides have been prepared by a number of strategies conducted either in solution or on solid supports. Excellent texts covering the basic principles and techniques are: *Principles of Peptide Synthesis,* Bodanszky. M., Springer-Verlag (1984); *Solid Phase Peptide Synthesis,* Stewart J. M., Young, J. D., Pierce Chemical Company (2nd. ed. 1984); and *The Peptides,* Gross, E., Meienhofer, J., Academic Press, Inc., (1979). The processes described herein, however, are not limited to the disclosure of these texts.

Synthetic cyclic peptides may be prepared in two phases. First, the linear peptide may be synthesized on a Milligen 9050 peptide or an ABI 431A synthesizer using 9-fluorenylmethyloxy-carbonyl (Fmoc) chemistry and side-chain-protected Fmoc-amino acid pentafluorophenyl esters which are known reagents or using derivatized Wang resin, Fmoc chemistry, and side-chain protected Fmoc-amino acid symmetrical anhydrides, prepared in situ, as reagents.

Second, the linear peptide may be cyclized, either in solution or with the peptide still attached to the solid phase resin. Cyclization may be accomplished by any technique known in the art, which may comprise, for example: a) incorporating cysteine residues into the linear peptide on either end of the sequence which is to form the loop and allowing disulfide bond formation under oxidizing conditions known in the art; b) preparing a cysteine containing peptide as in (a) but retaining the cysteines as free sulfhydryls (or as Acm protected thiols which are deprotected to the free sulfhydryls) and treating the peptide with o-xylylene dibromide or similar reagent, such as the diiodide, dichloride, or a dihalogenated straight or branched chain lower alkyl having between two and eight carbon atoms; such reagents react with the sulfur atoms of the cysteines to form a cyclic structure containing two nonlabile thioether bonds to the benzene or the alkyl; c) allowing a free group on one side of the loop amino acids to become amide bonded to a free carboxyl group on the other side of the loop amino acids through DPPA, BOP, or similar reagent mediated peptide bond formation. Each of these strategies is taken up in more detail below, after presentation of a generalized description of the cyclic peptides produced by these methods.

Thus, without limiting the coconjugate invention to the following peptides or methods of producing them, the PND peptides which may be conjugated after removal of appropriate protecting groups as necessary, according to this invention include those represented by the structure PEP, which includes the linear peptides of Table II above:

$$\text{r-}R^1\text{—N—}R^8\text{—C—C—}R^2\text{—GPGR—}R^3\text{—}R^4\text{—}R^5$$
$$\quad\quad\quad\quad\;\; | \quad | \quad \|$$
$$\quad\quad\quad\quad\;\; H \quad H \;\; O$$
$$\quad\quad\quad\quad\quad\quad\quad | \quad\quad\quad\quad\quad\quad\quad\quad\;\; |$$
$$\quad\quad\quad\quad\quad\quad\; R^2 \text{-----------------} R^7$$

wherein:

r is the position of linkage between PEP and OMPC, optionally comprising a marker amino acid, if $R^1$ is not a marker amino acid;

$R^1$ is:
 a) a bond, or
 b) an amino acid or a peptide of 2 to 5 amino acids, optionally including a marker amino acid which migrates at a position in the amino acid analysis spectrum which is isolated from the signal of the 20 naturally occuring amino acids; preferably norleucine, gamma aminobutyric acid, β-alanine, or ornithine;

$R^2$ is:
a) either a bond, an amino acid or a peptide of 2 up to 17 amino acids, or
b) a peptide of between 2 to 17 amino acids;

$R^3$ is:
 a) either a bond, an amino acid, or a peptide of 2 up to 17 amino acids, or
 b) a peptide of between 2 to 17 amino acids;

-GPGR- is the tetramer -GlyProGlyArg-; $R^2$ and $R^3$ cannot both be option (a);

$R^4$ is:
 a) —NH—CH—CO—, with $R^7$ bonded to the methine carbon, if $R^7$ is $R^8$, or
 b) a bond from $R^3$ to $R^7$ and $R^5$, if $R^7$ is carbonyl or —COCH$_2$CH$_2$CH(CONH$_2$)NHCO—;

$R^5$ is:
 a) an amino acid or a peptide of two to five amino acids, optionally including a marker amino acid,
 b) —OH,
 c) —COOH,
 d) —CONH$_2$,
 e) —NH$_2$, or
 f) -absent;

$R^6$ is:
 a) an amino acid side chain, selected from the side chain of any of the common L or D amino acids, (see table of Definitios and Abbreviations), if the optional bond (——————) to $R^7$ is absent,
 b) —$R^8$—S—S—, or —$R^8$—S—$R^8$—$R^9$—$R^8$—S—, if $R^7$ is $R^8$ or
 c) —$R^8$—NH— if $R^7$ is $$-\text{C}=\text{O, or } -\underset{\underset{\text{O}}{\|}}{\text{C}}-\text{CH}_2-\text{CH}_2-\underset{\underset{\text{CONH}_2}{|}}{\text{CH}}-\text{NH}-\text{C}=\text{O};$$

$R^7$ is:
 a) —$R^8$—,
 b) —C=O, or
 c)

$$-\underset{\underset{\text{O}}{\|}}{\text{C}}-\text{CH}_2-\text{CH}_2-\underset{\underset{\text{CONH}_2}{|}}{\text{CH}}-\text{NH}-\text{C}=\text{O};$$

$R^8$ is a bond or lower alkylene of between one and eight carbons;

$R^9$ is:
 a) $R^{10}$, or
 b) xylylene $R^{10}$ is:
 a) lower alkylene, or
 b) —CH$_2$O—CH$_2$; and every occurrence of a variable is independent of every other occurrence of the same variable. When a peptide has been synthesized with a protected amino terminal amino acid, the an amino terminal protecting group such as benzyloxy carbonyl (Z) for protecting amines, or acetamidomethyl (Acm) for protecting sulfhydryls, may be removed according to methods known in the art and exemplified herein. The deprotected group thus revealed may be utilized in covalent bond formation, through the linker r, to the immunogenic protein.

Hereinafter, amino acids —$R^2$—GPGR—$R^3$—, which form the "core" of the PND peptides, and go toward formation of the loop of a cyclic peptide, will be referred to as loop or core amino acids. When the optional bond between $R^6$ and $R^7$ is absent however, the structure, PEP, is linear, and encompasses all of the linear peptides of Table II.

Whether the peptide is linear or cyclic, the amino acid sequences comprising $R^2$ and $R^3$ of PEP may be any combination of amino acids, including sequences surrounding the core —GPGR— tetramer in any of the sequences of Table II. Thus, the core amino acids represented by —$R^2$—GPGR—$R^3$— may be further defined as having the core amino acid structure:

$$-X_nX_1X_2-\text{GPGR}-X_3X_4X_m-$$

wherein:

—GPGR— is the tetramer -GlyProGlyArg-;

$X_1$ is a constituent of $R^2$ selected from:

a) serine,
b) proline,
c) arginine,
d) histidine,
e) glutamine, or
f) threonine;

$X_2$ is a constituent of $R^2$ selected from:
a) isoleucine,
b) arginine,
c) valine, or
d) methionine;

$X_n$ is is a constituent of $R^2$ and is either a bond or a peptide of up to 15 amino acids;

$X_3$ is a constituent of $R^3$ selected from:
a) alanine,
b) arginine, or
c) valine;

$X_4$ is a constituent of $R^3$ and is selected from:
a) phenylalanine,
b) isoleucine,
c) valine, or
d) leucine;

$X_m$ is a constituent of $R^3$ and is a bond or a peptide of up to 15 amino acids. In a preferred embodiment of this invention X2 is isoleucine, such that the PND is that of the MN isolate of HIV. It is also feature of the preferred embodiment that the peptide contain a total of about 12–30 amino acid residues within the loop.

The cyclic peptides may be labile disulfide bonded structures or a cycle formed through a nonlabile bond or structure. The term "nonlabile bond" means a covalent linkage, other than a labile disulfide bond. Examples of such nonlabile bonds are amide and thioether bonds. These covalent linkages may be through a bridge structure, such as xylylene, through a lower alkyl, through —CH$_2$O—CH$_2$, or through an amino acid amide-bonded bridge. By altering the bridge structure and/or the number and combination of amino acids included in the peptide, the conformation of the loop structure of the cycle may be optimized, allowing for fine-tuning of the PND epitope presented to the immune system. For example, use of an o-xylylene bridge generates a "tighter" loop structure than when, for example, an eight carbon straight chain lower alkyl is used as the bridge. Thus, the conjugates of this invention are useful both as reagents to analyze the structure-function relationship of the PND epitope in raising anti-peptide, anti-HIV, HIV-neutralizing, and anti-AIDS immune responses in mammals, and as components for formulation of anti-HIV disease, including AIDS, vaccines.

Synthetic products obtained may be characterized by fast-atom-bombardment mass spectrometry [FAB-MS], reverse phase HPLC, amino acid analysis, or nuclear magnetic resonance spectroscopy (NMR).

a. Cyclic Peptides Through Disulfide-Bonded Cysteines

Peptides containing cysteine residues on either side of the loop amino acids may be cyclized under oxidizing conditions to the disulfide-bonded cycles. Methods for achieving disulfide bonding are known in the art. An example of disulfide bonding within this invention is given infra in Example 5, wherein cPND4 is produced. In that example, a process utilizing the Acm derivative of cysteine to generate disulfide bonded cPNDs is used, but other processes are equally applicable.

For example, in Example 43, CPND33 is prepared by highly diluting the linear peptide, having 2 free sulfhydryls, in trifluoroacetic acid. The peptide is allowed to form disulfides over 1 to 50 hours at between about 10° and 40° C. The disulfide bonded peptides are preferred.

Thus, in a preferred embodiment of this invention, the peptide has the structure:

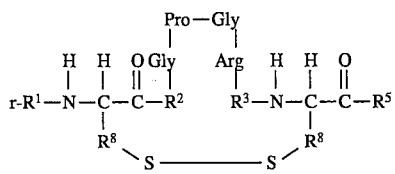

or pharmaceutically acceptable salts thereof, wherein:

r is:
a) hydrogen,
b)

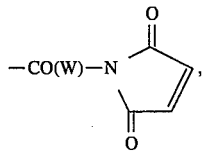

wherein W is preferably —(CH$_2$)$_2$— or —(CH$_2$)$_3$— or $R^6$, where $R^6$ is

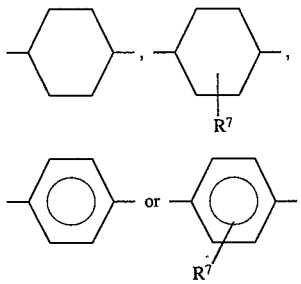

wherein $R^7$ is lower alkyl, lower alkoxy, or halo;

$R^1$ is:
a) a bond, or
b) an amino acid or a peptide of 2 to 5 amino acids, optionally including a marker amino acid;

$R^2$ is:
a peptide of 3 to 10 amino acids $R^3$ is:
a peptide of 3 to 10 amino acids —GPGR— is the tetramer -GlyProGlyArg-;

$R^5$ is:
a) —OH,
b) an amino acid or a peptide of 2 to 5 amino acids, optionally including a marker amino acid, or
c) —NH$_2$;

$R^8$ is lower alkylene of between one and eight carbons;

Lower alkylene consists of straight or branched chain alkyls having from one to eight carbons unless otherwise specified. Hereinafter, amino acids —R$^2$—Gly Pro Gly Arg—R$^3$—, which go toward formation of the loop of a cyclic peptide, will be referred to as loop amino acids.

In one embodiment of the invention, the cyclic peptide having the structure:

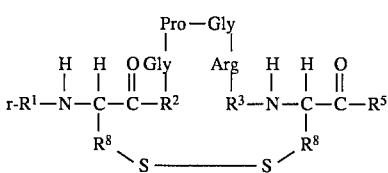

is prepared by cyclizing a linear peptide having the structure:

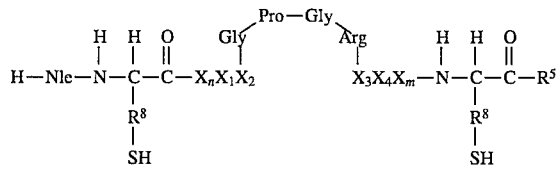

wherein:

—GPGR— is the tetramer -GlyProGlyArg-;

$X_1$ is a constituent of $R^2$ selected from:
 a) serine,
 b) proline,
 c) arginine,
 d) histidine,
 e) glutamine, which is preferred, or
 f) threonine;

$X_2$ is a constituent of $R^2$ selected from:
 a) isoleucine, which is most preferred,
 b) arginine, which is preferred,
 c) valine, or
 d) methionine;

$X_n$ is a constituent of $R^2$ and is an amino acid or a peptide of up to 8 amino acids;

$X_3$ is a constituent of $R^3$ selected from:
 a) alanine,
 b) arginine, or
 c) valine;

$X_4$ is a constituent of $R^3$ and is selected from:
 a) phenylalanine,
 b) isoleucine,
 c) valine, or
 d) leucine;

$X_m$ is a constituent of $R^3$ and is an amino acid or a peptide of up to 8 amino acids.

$X_2$ is preferably Isoleucine.

The novel disulfide bonded cyclic peptides used in this invention may be prepared in essentially two phases: First the linear peptide is synthesized on a Milligen 9050 or an ABI-431A peptide synthesizer using 9-fluorenyl-methyloxycarbonyl (Fmoc) chemistry and appropriately side-chain protected Fmoc-amino acid pentafluoro-phenyl esters as reagents or using derivatized Wang resin, Fmoc chemistry, and side-chain protected Fmoc-amino acid symmetrical anhydrides, prepared in situ, as reagents.

Second, the linear peptide is cyclized, either in solution or with the peptide still attached to the solid phase resin by incorporating cysteine residues into the linear peptide at either end of the sequence which is to form the loop, and oxidizing these to the disulfide. In a preferred embodiment, cyclization is accomplished by exposure of the peptide to (a) $H_2O_2$, (b) atmospheric oxygen, (c) aqueous $CH_3CN$ containing about 0.1–0.5% TFA, or (d) about 0.1M ferricyanide. The preferred method is exposure to atmospheric oxygen.

Products obtained may be characterized by fast atom bombardment-mass spectrometry [FAB-MS], reverse phase HPLC, amino acid analysis or nuclear magnetic resonance spectroscopy (NMR).

Thus, the peptides useful in this invention may be prepared as further described below in (i) and (ii):

i. Peptide Cyclization in the Solid State

A linear peptide containing $C^1$ and $C^2$ on either side of the loop amino acids, where $C^1$ and $C^2$ are both cysteine or another amino acid containing free sulfhydryl groups in the side chain, is prepared according to known synthetic procedures (see discussion supra). In the completed cyclic PND, the sulfhydryl containing side chains, (—$R^8$—SH), go toward making up the —$R^8$—S— groups of the completed cyclic HIV PND structure shown above. Amino acids to be incorporated which have reactive side chains (R groups) are used in an appropriately R-group protected form. For example, histidine is triphenylmethyl (Trt), or Boc protected, and arginine is 4-methoxy-2,3,6-trimethylphenyl sulfonyl (Mtr) protected.

Preferably, a resin is purchased with $C^2$ in its Acm protected form already attached to the resin, for example, Fmoc-L-Cys(Acm)-O-Wang resin. The cysteine incorporated at the amino terminal side of the loop amino acids, $C^1$, may also be the Acm derivative. Either $C^1$ or $C^2$ may be bound to additional amino acids, $R^1$ or $R^5$ respectively, which may be utilized in the formation of conjugates with carrier molecules or may serve as marker amino acids for subsequent amino acid analysis, such as when norleucine or ornithine is used.

The sulfur of the acetamidomethylated cysteines are reacted, at room temperature for about 15 hours in a solvent compatible with the resin, as a 1–50% concentration of an organic acid, preferably about 10% acetic acid in anhydrous dimethylformamide (DMF), with about a four fold molar excess of a heavy metal salt, such as mercuric acetate [$Hg(OAc)_2$] for each Acm group. The resulting heavy metal thioether, for example the mercuric acetate thioether of the peptide, PEP(S—HgOAc), is then washed and dried. Addition of excess hydrogen sulfide in DMF yields insoluble metal sulfide, e.g. mercuric sulfide (HgS), and the peptide with free sulfhydryl groups. The free sulfhydryls are then oxidized by one of the aforementioned methods. Alternatively, the Acm protected thiols may be converted directly to the cyclic disulfide by treatment with iodine in a methanol/DMF solvent.

ii. Cyclization of Peptides in Solution

Essentially the same process described above for solid state cyclization applies with two main variants: If the peptide is cleaved (95% TFA/4% ethanedithiol/1% thioanisole) from a pepsyn KA resin, acid labile side chain protecting groups are also removed, including Cys(Trt) which provides the necessary free —SH function. If however, Cys(Acm) protection is used, then mercuric acetate/hydrogen sulfide cleavage to the free —SH group is required as an independent procedure, with the linear peptide either on or off the resin.

One method however, is the use of Cys(Acm) protection and Sasrin or Pepsyn KH resin, and cleavage of the linear, fully protected peptide from the resin with 1% TFA/$CH_2Cl_2$. Mercuric acetate/hydrogen sulphide then selectively converts Cys(Acm) to the free —SH group, and cyclization is effected on the otherwise protected peptide. At this point, the peptide may be maleimidated in situ, selectively on the N-terminus. Acid labile side chain protecting groups are cleaved with 98% TFA/2% thioanisole, and the cyclic peptide is isolated by HPLC. The preferred method, however, is to cleave the peptide from the resin, and allow cyclization by one of the aforementioned methods. The most preferred method is to allow air oxidation for about one to fifty hours of between 10° and 40° C.
Thus, in a particularly preferred embodiment of this invention, a peptide (cPND 33) having the structure (SEQ ID: 1:):
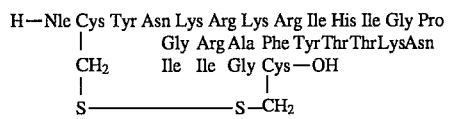
is conjugated to OMPC through either the amino terminal Nle or one of the internal lysines to generate one or a mixture of all of the structures:
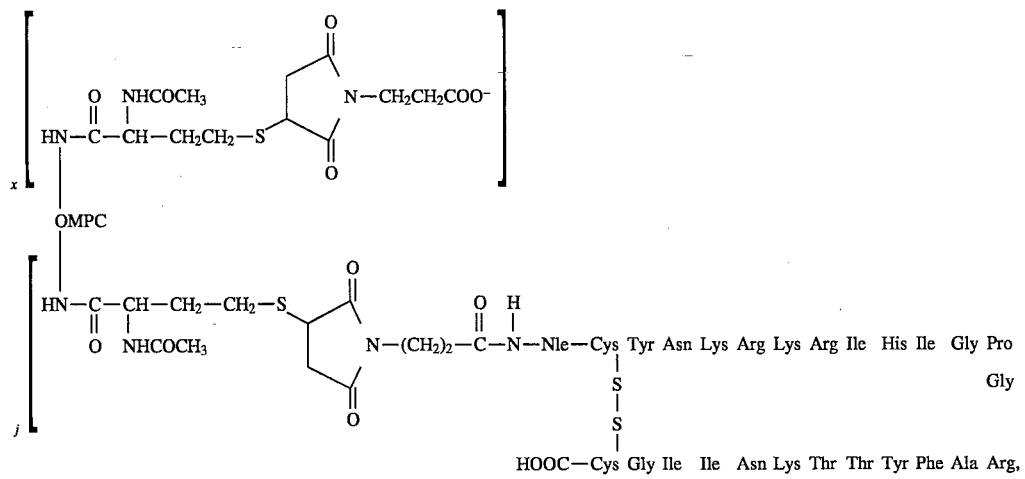
e-1)
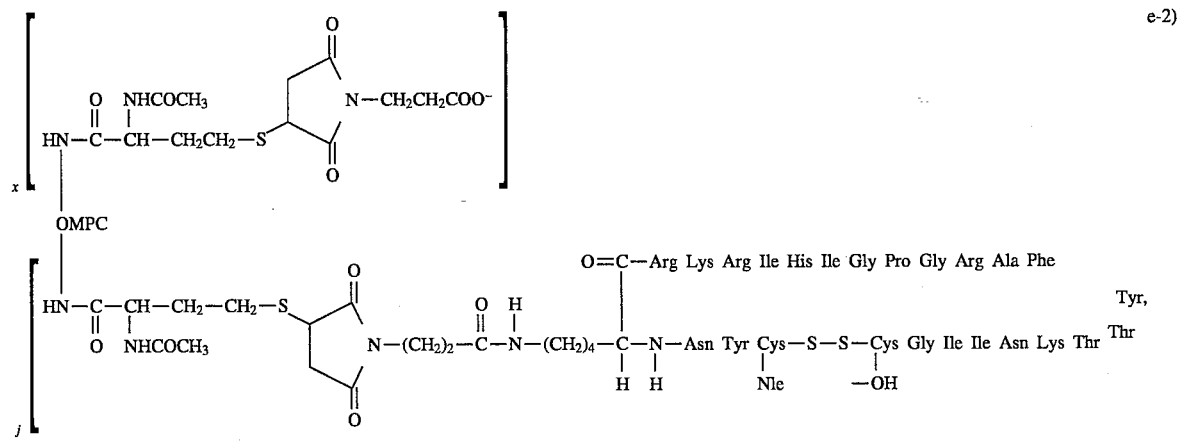
e-2)
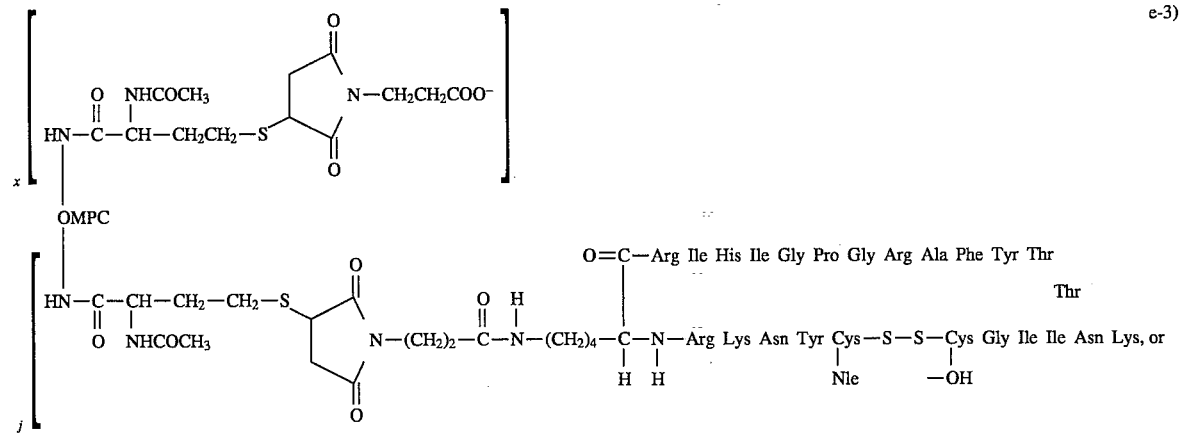
e-3)

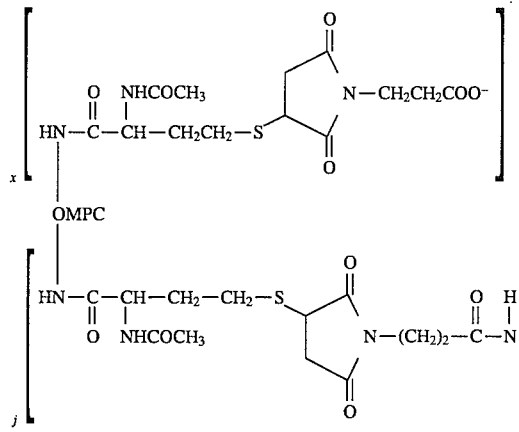
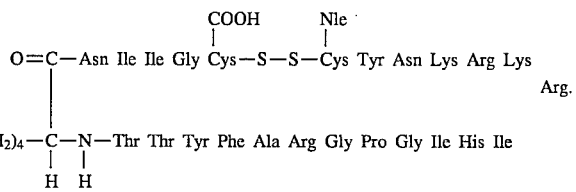

or pharmaceutically acceptable salts thereof, wherein:

j is the percentage by mass of peptide in the coconjugate, and is preferably between 1% and 50% of the total protein mass in the conjugate;

x is the number of moles of low molecular weight residues containing anionic substituents and is preferably between 1% and 90% of m, and most preferably between 10% and 50% of m; and m is the molar amount of reactive nucleophilic functionalities in the immunogenic protein, PRO, prior to conjugation, are useful for inducing anti-peptide immune responses in mammals, for inducing HIV-neutralizing antibodies in mammals, for formulating vaccines to prevent HIV-disease or infection, or for treating humans afflicted with HIV-disease or infection, including AIDS and ARC.

b. Cyclic Peptides through Thioether Linkage to o-Xylylene or Lower Alkyls i. Peptide Cyclization in the Solid State A linear peptide containing $C^1$ and $C^2$ on either side of the loop amino acids, where $C^1$ and $C^2$ are both cysteine or another sulfhydryl containing amino acid, is prepared according to known synthetic procedures (see discussion supra). In the completed cylic PND, $C^1$ and $C^2$ become part of the $R^6$ and $R^7$ groups of the PEP structure shown above. Amino acids to be incorporated which have reactive side chains (R groups) are used in an appropriately R-group-protected form. For example, histidine is triphenylmethyl- (Trt) protected, arginine may be 4-methoxy-2,3,6-trimethylphenyl sulfonyl (Mtr) protected. [*Principles Of Peptide Synthesis*, Bodanszky. M., Springer-Verlag (1984); *Solid Phase Peptide Synthesis*, Stewart 3. M., Young, J. D., Pierce Chemical Company (2nd. ed. 1984); and *The Peptides*, Gross, E., Meienhofer, J., Academic Press, Inc., (1979)].

Preferably, a resin is purchased with $C^2$ in its Acm-protected form already attached to the resin, for example, Fmoc-L-Cys(Acm)-O-Wang resin. The cysteine incorporated at the amino terminal side of the loop amino acids, $C^1$ may also be the Acm derivative. Either $C^1$ or $C^2$ may be bound to additional amino acids, $R^1$ or $R^5$ respectively, which may be utilized in the formation of conjugates with carrier molecules or may serve as marker amino acids for subsequent amino acid analysis, such as when norleucine or ornithine is used.

The sulfur of the acetamidomethylated cysteines is reacted, at room temperature for about 15 hours in a solvent compatible with the resin, such as 10% acetic acid in anhydrous dimethylformamide (DMF), with about a four-fold molar excess of a heavy metal salt, such as mercuric acetate [Hg(OAc)$_2$] for each Acm group. The resulting heavy metal thioether, for example the mercuric acetate thioether of the peptide, PEP(S—HgOAc), is then washed and dried. Addition of excess hydrogen sulfide in DMF yields insoluble metal sulfide, e.g., mercuric sulfide (HgS), and the peptide with free sulfhydryl groups.

A mixture of about an equimolar amount, as compared with peptide, of o-xylylene dibromide or dichloride, a dibrominated or dichlorinated lower alkyl, 1,3-dihalogenenated —CH—O—CH—, or similar reagent which will provide a desirable bridge length, is added to the derivatized resin. A large excess of tertiary amine, preferably triethylamine (NEt$_3$) in DMF is added slowly. The reaction with the bis-sulfhydryl peptide moiety is allowed to proceed for about sixteen hours at room temperature, yielding the bridge group derivatized cyclic peptide bound to resin. Deprotection of acid sensitive side chain protecting groups and cleavage from the resin is achieved by treatment with 95% trifluoroacetic acid (TFA) in the presence of 4% 1,2-ethanedithiol and 1% thioanisole. The dissolved cyclic peptide may then be separated from the resin by filtration. The filtrate is evaporated and the crude residual product is purified by high performance liquid chromatography (HPLC) according to known methods, for example by reverse phase HPLC.

ii. Cyclization of Peptides in Solution

Essentially the same process described above for solid state cyclization applies with two main variants: If the peptide is cleaved (95% TFA/4% ethanedithiol/1% thioanisole) from a pepsyn KA resin, acid labile side chain protecting groups are also removed, including Cys(Trt) which provides the necessary free —SH function. If however, Cys(Acm) protection is used, then mercuric acetate/hydrogen sulfide cleavage to the free —SH group is required as an independent procedure, with the linear peptide either on or off the resin.

The preferred method however, is the use of Cys(Acm) protection and Sasrin or Pepsyn KH resin, and cleavage of the linear, fully protected peptide from the resin with 1% TFA/CH$_2$Cl$_2$. Mercuric acetate/hydrogen sulphide then selectively converts Cys(Acm) to the free —SH group, and cyclization is effected on the otherwise protected peptide. Acid labile side chain protecting groups are cleaved with 95% TFA/4% ethanedithiol/1% thioanisole, and the cyclic peptide is isolated by HPLC.

Removal of excess reagents, such as unreacted xylylene dibromide, prior to acid cleavage of the protecting groups is conveniently achieved by, for example, a step gradient reverse phase HPLC run prior to more selective gradient elution.

Cyclic HIV PND peptides prepared according to the method of this subsection include, but are not limited to, the sample cPNDs represented below. The methods of this subsection are generally applicable to small peptides, and particularly applicable to peptides of between 5 and 30 amino acids. An optimal ring size may include between 5 and 10 amino acids, including the —GPG—trimer, and this ring size is easily maintained by production of cycles from linear peptides having the appropriate number and combination of amino acids.

Representative peptides resulting from the process described in this subsection b. parts (i). and (ii) are shown below. The coconjugate invention should, however, not be construed as being limited to use these particular embodiments of HIV cyclic PND peptides. Other linear HIV PND peptide sequences may be cyclized in essentially the same fashion used to provide these peptides. Series of peptides having divergent primary sequences could be generated and would be beneficial in this invention as long as they continue to elicit an anti-peptide, anti-HIV, or HIV-neutralizing immune response.

| Name | Structure |
|---|---|
| cPND1 | H—Nle—C—H—I—G—P—G—R—A—F—C—OH with S—CH$_2$—C$_6$H$_4$—CH$_2$—S bridge |
| cPND2 | H—Nle—C—I—G—P—G—R—A—F—C—OH with S—CH$_2$—C$_6$H$_4$—CH$_2$—S bridge |
| cPND3 | H—Nle—C—R—I—Q—R—G—P—G—R—A—F—V—T—C—OH with S—CH$_2$—C$_6$H$_4$—CH$_2$—S bridge | c. Cyclization Through Amide Bond Formation

Novel amide bonded cyclic HIV PND peptides may be prepared for conjugation in essentially two phases: First, the linear peptide is prepared, for example on an ABI-431A peptide synthesizer, by known solid phase peptide synthetic chemistry, for example using Fmoc chemistry and appropriately side-chain protected Fmoc-amino acids as reagents.

Second, the linear peptide is cleaved from the resin and cyclized in solution by allowing the free amino terminus of the peptide, the free amino group of an amino terminal isoglutamine, or a free ε-amino or α-amino group of a lysine on one side of the loop amino acids to be amide bonded to a free carboxyl group on the carboxy-terminal side of the loop amino acids through DPPA, BOP, or similar reagent mediated peptide bond formation.

Products obtained may be characterized by fast atom bombardment-mass spectrometry [FAB-MS], reverse phase HPLC, amino acid analysis, or nuclear magnetic resonance spectroscopy (NMR).

Thus, highly preferred embodiments of this invention are coconjugates having a first set of covalent linkages from OMPC to maleimidopropionic acid, maleimidoethanephosphonic acid, maleimidoethanesulfonic acid, maleimido-glutaric acid, or maleimido-succinic acid, and a second set of covalent linkages from OMPC to an amide bonded cyclic HIV PND, prepared as described hereinabove. Where the PND is from an predominant isolate, such as the HIV IIIB or the HIV MN isolate, a coconjugate vaccine, or a mixture of such coconjugate vaccines is highly advantageous for prophylaxis or treatment of AIDS or ARC. Examples of such preferred embodiments having the structure:

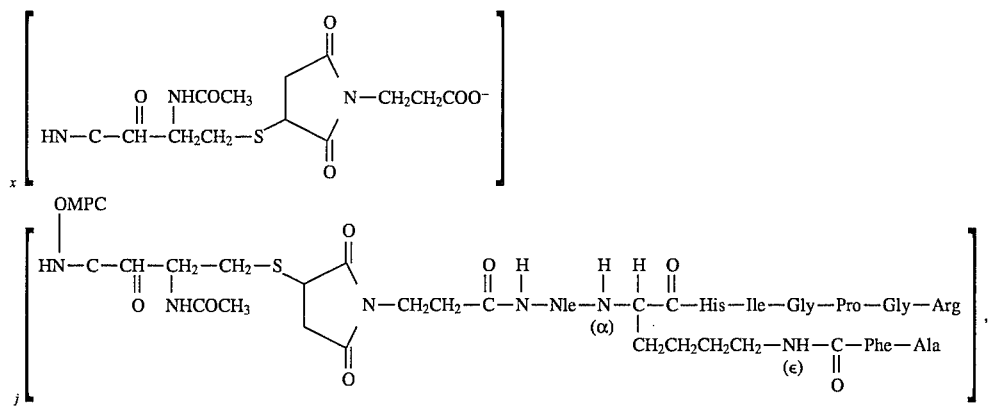
a)
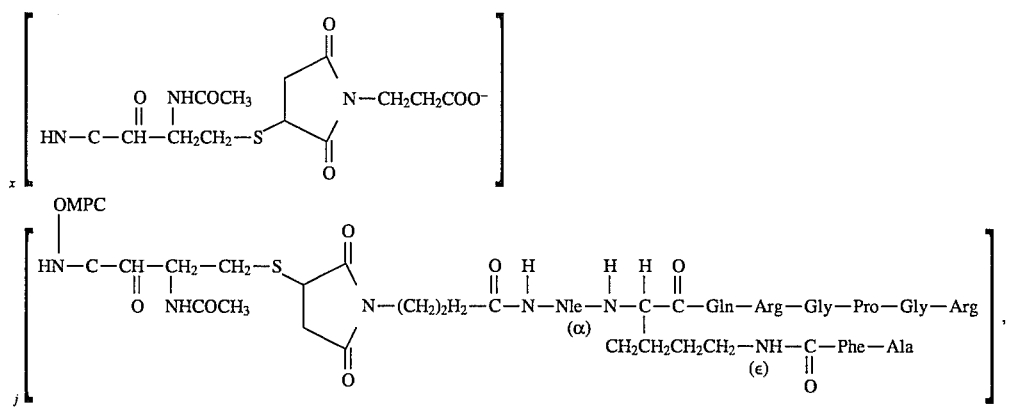
b)
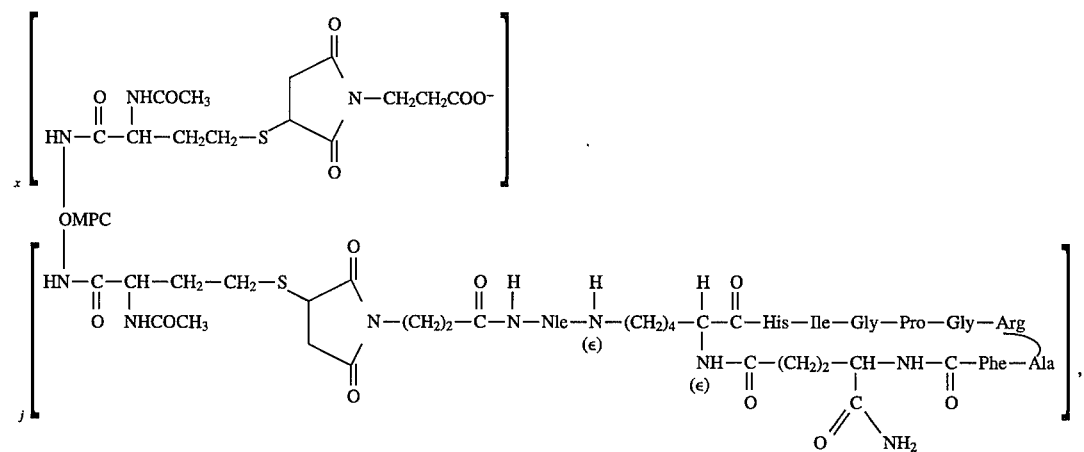
c)

d)
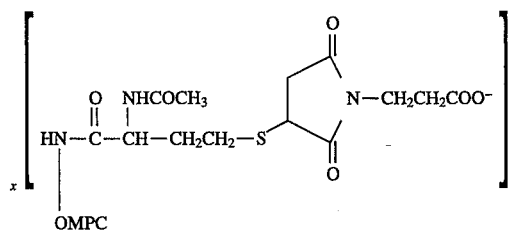
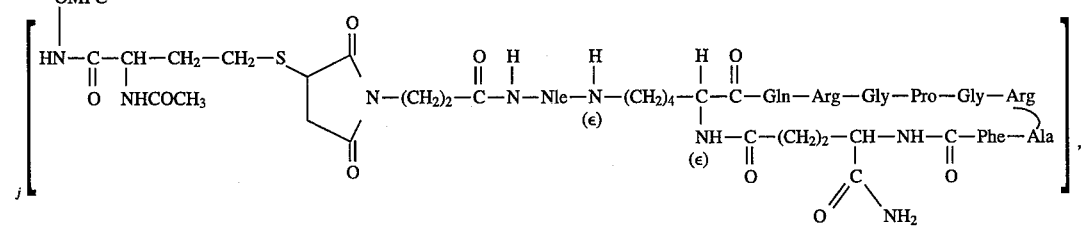
e-1)
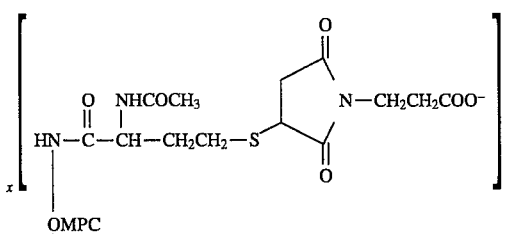
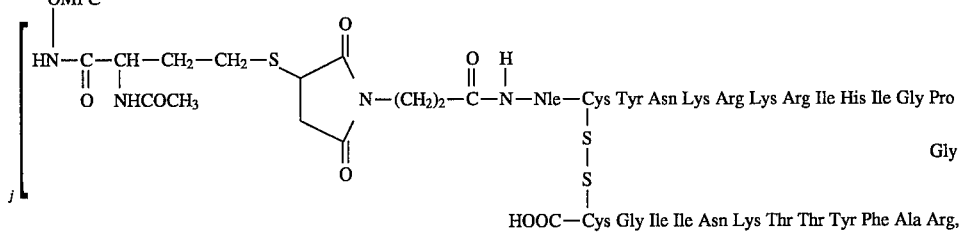
e-2)
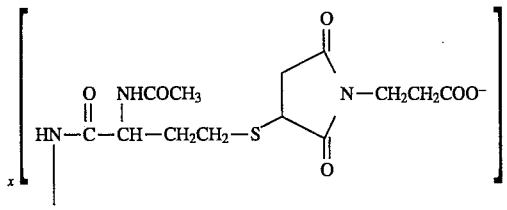
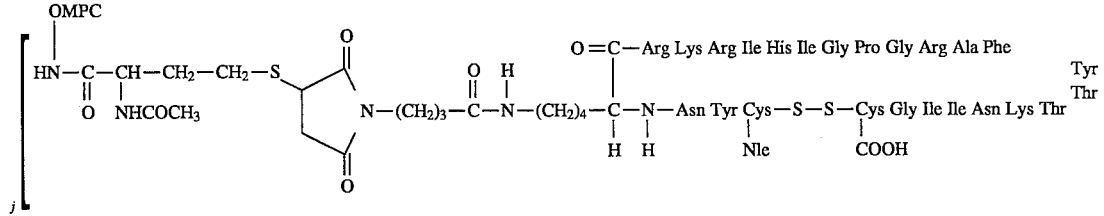

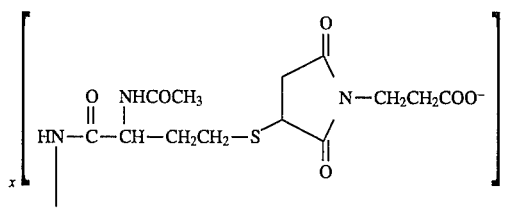

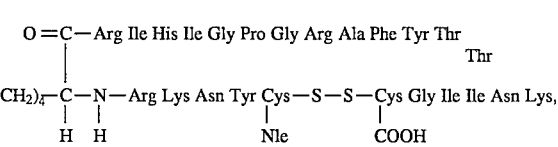

or

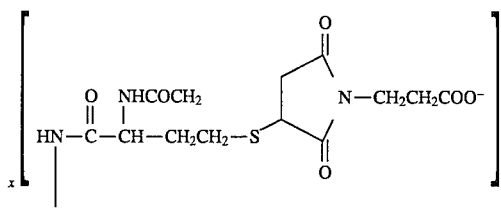

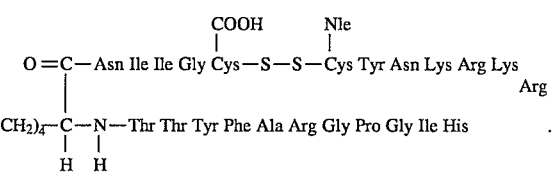

or pharmaceutically acceptable salts thereof, wherein:

j is the percentage by mass of peptide in the coconjugate, and is preferably between 1% and 50% of the total protein mass in the conjugate;

x is the number of moles of low molecular weight residues containing anionic substituents and is preferably between 1% and 90% of m, and most preferably between 10% and 50% of m; and m is the molar amount of reactive nucleophilic functionalities in the immunogenic protein, PRO, prior to conjugation, are useful for inducing anti-peptide immune responses in mammals, for inducing HIV-neutralizing antibodies in mammals, for formulating vaccines to prevent HIV-disease or infection, or for treating humans afflicted with HIV-disease or infection, including AIDS and ARC.

The following examples are provided to more particularly demonstrate how to make and use the coconjugate of this invention. However, the examples provided are not to be construed so as to limit the scope of the invention.

A. Examples of Peptide Preparations

EXAMPLE 1

Solution Cyclization to Form cPND1

Anhydrous DMF (20 ml) was degassed and HPLC-isolated linear 11-mer H-NleCHIGPGRAFC-OH (20 mg, 17 µmole) was dissolved and sealed under a nitrogen atmosphere. A solution of o-xylylene dibromide (4.7 mg, 17.9 µmole) in anhydrous DMF (50 µl) was added. Next, NEt$_3$ (11.9 µl, 85.2 µmole) in DMF was added over a period of about 6.5 hours. About one hour after complete addition of the base, the solution was dried. The residue was resuspended in ether, centrifuged to spin down the insoluble product, and then redried. An aliquot analyzed by fast atom bombardment-mass spectrometry (FAB-MS) yielded a major ion [M+H]$^+$ of 1275. Isocratic reversed-phase HPLC on a Vydac C18 column (0.46×25.0 cm) using 0.1% TFA/ 24% CH$_3$CN at 2.0 ml/minute, monitored at 215 nm, showed a sharp product peak having a retention time of about 18.5 minutes. A preparative scale isolation was run over 135 minutes at 10 ml/minute from 24–29% CH$_3$CN, and the product with a retention time of 76.41 minutes under these conditions was collected and rechromatographed under analytical conditions to confirm its identity. Amino acid analysis and 400 MHz NMR analyses were consistent with the structure cPND1:

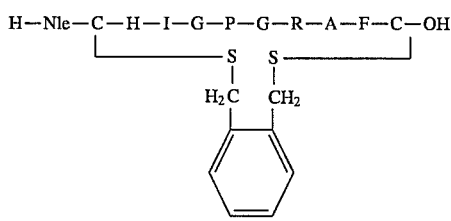

EXAMPLE 2

Solution Cyclization to Form cPND2

The procedure described in Example 1 was followed except that the linear 10-mer H-Nle-CIGPGRAFC-OH (20 mg, 19.3 µmole) was used. After the addition of base, the solution was kept under nitrogen for an additional 9 hours. FAB-MS yielded [M+H]⁺=1138 and [M+Na]⁺=1160, consistent with the structure proposed for cPND2. Preparative HPLC using two 2.12×25 cm Vydac C18 columns was conducted over 90 minutes from 24% to 28 % CH₃CN/0.1% TFA, at 10 ml/minute. The eluate was monitored at 215 nm and two product peaks at retention times of 63.42' and 70.82' were collected, dried, and subjected to FAB-MS. Both materials had [M+H]⁺ of 1138, (the later peak also had a [M+Na]⁺ of 1160) which is consistent with the structure cPND2:

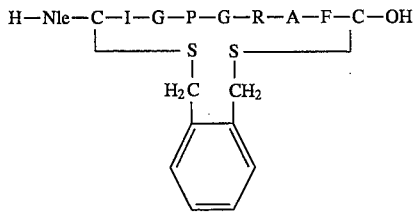

EXAMPLE 3

Solution Cyclization to Form cPND3

The same procedure used in Examples 1 and 2 was employed here except that the linear 15-mer H-Nle-CRIQRGPGRAFVTC-OH (21.2 mg, 11.92 µmole) was used, and NEt₃ was added over about 10 hours. An additional 5-hour exposure to base was permitted prior to analysis by analytical HPLC. FAB-MS of the crude product showed a single intense [M+H]⁺ of 1779 which is consistent with the structure of cPND3:

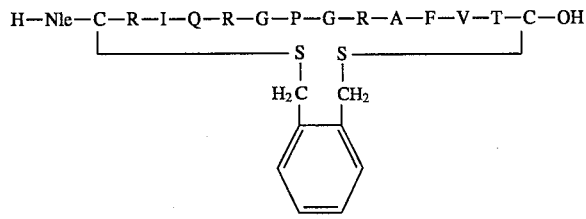

EXAMPLE 4

Solid State Cyclization to Form cPND1

A linear PND peptide was prepared on Wang resin on an ABI-431A peptide synthesizer, starting from Fmoc-L-Cys(Acm)-O-Wang resin (0.61 meq/gram). Fmoc chemistry and Fmoc-amino acid symmetrical anhydrides (4× excess, prepared in situ) were used as reagents on a 0.25 mmole scale to generate 745 mg of the peptide:

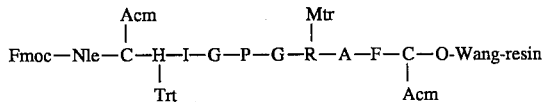

Hg(OAC)₂ (64 mg, 0.2 mmole) was dissolved in 10% acetic acid in DMF (0.5 ml) and added to the dried resin (149 mg, 0.05 meq) shown above. More 10% acetic acid in DMF (0.2 ml) was added to the swollen resin, and the solution was stirred overnight. Thereafter the resin was filtered, washed with DMF (5×1 ml), CH₂Cl₂ (3×1 ml), and ether (3×2 ml). Subsequently, the resin was dried and 1 ml H₂S saturated DMF was added, followed by a second aliquot of the same.

The resin was then filtered and washed as above and then dried, yielding a black resinous powder (179 mg).

A mixture of o-xylylene dibromide (3.2 mg) and NEt₃ (3.4 µl) in DMF (2 ml) was added to the resin (35 mg) at room temperature, and allowed to react for 16 hours. The resin was filtered, washed as above, and dried. The Fmoc was removed by treatment with 20% piperidine in DMF (1 ml) over 20 minutes at room temperature. The resin was washed again as above, and dried.

The cPND1 peptide was cleaved from the resin, and Trt and Mtr protecting groups concomitantly removed, by treating with 95% TFA/4% ethane dithiol/1% thioanisole (1 ml) at room temperature over 6 hours. The solution was filtered, the resin washed with additional 100% TFA (3×1 ml), and the combined filtrate was evaporated at 20° C./0.1 mm pressure. Material that was insoluble in ether was removed by extraction (3×2 ml) and the insoluble crude product was redried at 20° C./0.1mm pressure.

Analytical HPLC using a 0.46×25 cm Vydac C18 column was used to identify the product. Comparison with the product obtained from Example 1 confirmed that authentic product was present (retention time of 12.88' as compared with 12.97'). Preparative HPLC was conducted over 90 minutes from 25% to 30% CH₃CN/0.1% TFA at 10 ml/minute using two 2.12×25 cm Vydac C18 columns in series. The peak eluting at 54.12' was collected. Co-chromatography, on an analytical scale, of this material with material prepared in Example 1 showed a single sharp peak. FAB-MS had a [M+H]⁺ of 1275, confirming the preparation of cPND1 (see Example 1 above for structure).

EXAMPLE 5

Solid State Synthesis of Disulfide-Bonded CPND4

A linear PND peptide was prepared on Wang resin using an ABI-431A peptide synthesizer, starting from Fmoc-L-Cys(Acm)-0-Wang resin (0.61 meq/gram). Fmoc chemistry and Fmoc-Amino Acid symmetrical anhydrides (4× excess, prepared in situ) were used as reagents on a 0.25 mmole scale to generate 745 mg of the peptide:

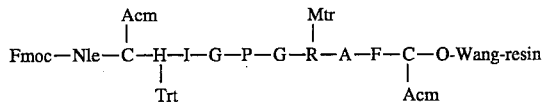

A solution of iodine in 5% methanol/anhydrous DMF (1 ml) was added to the dried, derivatized Wang resin shown above and stirred at room temperature for 4 hours. The resin was filtered, washed with anhydrous DMF (5×2 ml), and finally resuspended in DMF (2 ml). Two drops of a 0.1M solution of sodium thiosulphate in water were added, and stirred for a few seconds. The resin was washed with aqueous 95% DMF (3×2 ml), anhydrous DMF (2 ml), methylene chloride (3×2 ml), ether (3×2 ml) and dried.

The Fmoc and other protecting groups were removed by treatment with 20% piperidine in DMF over 20 minutes, and the resin was washed and dried. The resin was cleaved from the disulfide bonded cyclic peptide by treatment with 95% TFA/4% ethane dithiol/1% thioanisole (1 ml) at room temperature for 6 hours. The solution was filtered, the resin washed with additional 100% TFA (3×1 ml), and the combined filtrate dried. Material that was insoluble in ether was removed by extraction (3×2 ml) and the solution redried.

Preparative HPLC using two 2.12×25 cm Vydac C18 reverse phase columns in series and a gradient elution of 20 to 24% CH$_3$CN over 90' allowed isolation of a sharp peak eluting at 36.66' under these conditions. Analytical HPLC yielded a single peak upon co-chromatography of a known disulfide bonded cyclic standard with the product obtained from preparative HPLC. FAB-MS gave a [M+H]$^+$ of 1171, which is consistent with the the disulfide bonded cyclic structure cPND4:

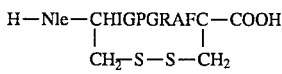

EXAMPLE 5-b

1. Synthesis of: H-Nle Cys Tyr Ash Lys Arg Lys Arg Ile His Ile Gly Pro Gly Arg Ala Phe Tyr Thr Thr Lys Ash Ile Ile Gly Cys-OH
($C_{135}H_{220}N_{42}O_{33}S_2$, formula weight=3023.6)

The 26 mer was assembled on the Milligen #9050 synthesizer, starting from the partially racemised Fmoc-L-Cys(Trt)-OPKA resin (Milligen batch B 090426) using 0.081 meq/g (about 604 mg), using 2.47 g (0.200 meq). The resin was mixed with an equal volume of glass beads (Sigma 150–212 μm). The mixture completely filled two 1×10 cm columns, connected in series. Reagents were Fmoc-Pft ester (except for threonine, which was dHBt), using in four fold molar excess in N-methyl pyrrolidine solvent. Side chain protection was: Y (tert-butyl); K (Boc); R (Mtr); His (Boo); T (tert-butyl); C (Trt). The protocol was modified to give double coupling with K$^7$; I$^9$; I$^{11}$; G$^{12}$; p$^{13}$; G$^{14}$; R$^{15}$; F$^{17}$; Y$^{18}$; T$^{19}$; T$^{20}$; I$^{73}$; I$^{24}$. Acylation recycle times were extended from 30 to 60 minutes for all units, except for G$^{14}$ and A$^{16}$, and to 90 minutes for I$^9$ (2×); I$^{11}$ (2×); I$^{23}$ (2×) and I$^{24}$ (2×). The derivatized resin was maintained as the free terminal amine which was washed with CH$_2$CL$_2$ and air-dried.

The mixture of dry derivatized resin and glass beads was resuspended in 95% TFA, 4% ethane dithiol, 1% CH$_3$SPh (30 mL) at 23° C. in a sealed flask, with gentle stirring on an oscillating tray for 8 hours. The bright yellow mixture was then filtered and the insolubles were thoroughly extracted with 100% TFA (3×20 mL). The combined dark orange filtrated were evaporated to give a pale tan, oily gum. On trituration with ether (20 mL) this material instantly became a colorless solid, which was transferred to a filter by triturating with additional ether (3×20 mL). After drying, the crude product was obtained as a fine colorless powder (583 mg).

Analytical reverse phase HPLC on a 0.46×25.0 cm Vydac C$_{18}$ column of about a 50 μg sample, dissolved in aqueous 0.1% TFA/20% CH$_3$CN, revealed a major component and a later eluting minor component. These were separately collected after injection of a 30 mg and another 50 mg aliquot of the sample onto two 2.21×25.0 cm preparative columns in series. A total of 35.2 mg of the earlier eluting material and 8.2 mg of the later eluting material was recovered following lyophilization. FAB-MS gave a [M+H]$^+$=3022.1 and an [M+Na]=3044.2, which correlates with the calculated mass.

2. Preparation of the Cyclic Disulfide

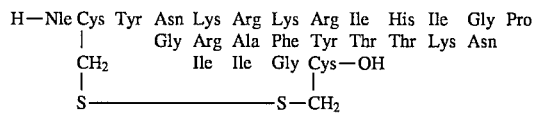

a. K$_3$Fe(CN)$_6$ Induced Oxidation

The linear 26 mer dithiol compound (35.0 mg) was dissolved in degassed distilled water (38 mL) at 23° C. to give a clear colorless solution at pH 2.73. The pH was adjusted to 8.5 with 0.1N NH$_4$OH, and the solution was covered with an atmosphere of nitrogen. An aliquot of the material was immediately run on analytical reverse phase HPLC and found to be undergoing oxidation as evidenced by the appearance of a early peak.

With magnetic stirring, a freshly prepared solution of 0.01M K$_3$Fe(CN)$_6$ was added by power driven hypodermic syringe at 23° C. under nitrogen. Analysis of a small aliquot by HPLC revealed total conversion of starting material to an earlier elution time. The reaction mixture (pH 8.3) was mixed with 10% aqueous acetic acid and stirred to give a pH of 4.0. The solution was filtered to remove insoluble material, and the faintly yellow solution was evaporated and then lyophilized ti give about 27.9 mg of a pale yellow powder. The material was dissolved in 0.1% TFA, 20% CH$_3$CN and gradient eluted on a preparative HPLC. A major early eluting peak and a later eluting peak (4:1) were separately collected, lyophilized to yield 6.1 mg of the early and 1.5 mg on the late eluting materials. FAB-MS analysis of the early eluting material: [M+H]$^+$ 3019.7; [M+Na]$^+$ 3024.5; FAB-MS analysis of the late eluting material: [M+H]$^+$ 3021.0; [M+Na]$^+$ early material=3041.5; all of which corresponds to the correct mass for the cyclized cPND33. The later eluting material is the D-cysteine isomer.

Amino acid analysis of the product gave the predicted amino acid compositions for the cyclized products and confirmed that the later eluting material is the D-cyteine containing diastereomer.

b. Air Oxidation

The linear 26 mer prepared in (1) above (86 mg, 28.4 μmoles) was dissolved in aqueous 0.1% TFA, 20% acetonitrile (284 mL) at 23° C. and the solution was allowed to stand open to the air. Cyclization was monitored by reverse phase HPLC and the sample was found to be almost completely converted to the early eluting material, with almost complete disappearance of starting linear material, by t=24 hours. The clear, colorless solution was evaporated to about 8 mL at which point an additional 10 mg sample prepared in the same way as the 86 mg, was added. The combined sample was evaporated to about 9 mL. The cloudy colorless solution was subjected to HPLC separation, in two separate runs, on two 2.21×25.0 cm Vydac C$_{18}$ columns in series. Two peaks of material were separately collected, an early eluting peak and a later eluting peak. Each peak was separately evaporated and lyophilized to yield 30.1 mg and 9.7 mg of the early and late materials respectively. The early eluting material was combined with other preparations of early eluting cyclized material to yield a total of 47.5 mg of a faintly blush fluffy powder. Analytical HPLC of this material gave a single peak.

EXAMPLE 6

Solution Synthesis of Peptide Bonded cPND7

The linear peptide Cbz-Nle-Lys(Boc)-His(Trt)-Ile-Gly-Pro-Gly-Arg(Mtr)-Ala-Phe was synthesized following solid-phase methods on an ABI 431A peptide synthesizer using 373 milligrams (0.1 mmoles) of commercially available Fmoc-Phenylalanyl-p- alkoxybenzyl alcohol resin. With the exception of norleucine, which was purchased in the benzyloxycarbonyl (Cbz) protected form, L-amino acids used were the fluorenylmethoxycarbonyl (Fmoc) derivatives having the appropriate acid-labile side chain protecting groups. The polypeptide-derivatized resin product was transferred to a sintered glass funnel, washed with dichloromethane, and dried, to yield 0.6 g of polypeptide-resin product.

The peptide was cleaved from the resin by treatment with 6 ml of a 95:2:3 mixture of TFA:1,2 ethanediol:anisole for 16 hours. The reaction mixture was filtered through a sintered glass funnel, the resin washed with 10 ml TFA, and the filtrates combined. Following concentration to about 1 to 2 ml of yellow oil, the linear peptide was recovered by trituration with 400 ml of diethyl ether, in 50 ml portions, and filtration on a sintered glass funnel. Dissolution with 100 ml 1% TFA followed by lyophilization yielded 298 mg of linear peptide.

The peptide powder was dissolved in 800 ml DMF, neutralized with 0.42 ml diisopropylethylamine, and treated with 0.077 ml diphenylphosphorylazide. The solution was stirred in the dark for 70 hours at 4° C. to allow formation of the cyclic lactam. After quenching by addition of 3 ml glacial acetic acid, the reaction mixture was concentrated to about 1 to 2 ml of oil, dissolved in 10% aqueous acetic acid, and lyophilized.

The cyclic peptide was purified by G-15 size exclusion chromatography using 5% acetic acid as the mobile phase. Fractions, monitored by UV detection, containing the peptide were pooled and lyophilized to yield 135 mg of dry cyclic peptide. All results obtained were consistent with the structure cPND7:

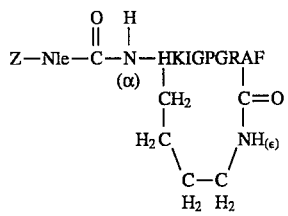

which may also be represented as:

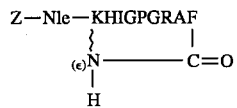

EXAMPLE 7

Deprotection of cPND7 to Yield the Hydrogen Form, cPND8

Deprotection of cPND7 was achieved by dissolving the cyclic peptide in 20 ml of 30% aqueous acetic acid and hydrogenation at 40 psi for 16 hours over 100 mg of 10% palladium on carbon. The reaction mixture was filtered over celite to remove the catalyst, and the filtrate was lyophilized. Reverse phase HPLC using a Vydac C18 semi-prep column was utilized to obtain 8.5 mg of pure deprotected cyclic peptide. This method of deprotection is applicable to all peptides synthesized as the benzyloxycarbonyl N-protected peptide, to yield the free hydrogen form of the peptide which may now be activated at the amino terminus in preparation for conjugation. The structure of the product was confirmed by FAB-MS, analytical HPLC and amino acid analysis, and all results were consistent with the structure cPND8:

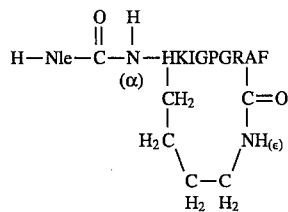

which Fay also be represented as:

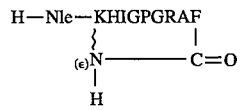

EXAMPLE 8

Synthesis of cPND10

The synthesis of cPND10, having an Acm protected Ac-cysteine at the peptide amino-terminus, is identical to the procedure used in Example 1, except that the synthesis here included an Fmoc-norleucine, rather than the Z-Nle, and the additional amino acid, Ac-Cys(Acm) was used as the N-terminal amino acid. Thus, the linear peptide Ac-Cys(Acm)-Nle-Lys(Boc)-His(Trt)-Ile-Gly-pro-Gly-Arg(Mtr)-Ala-Phe, was assembled using commercially available Fmoc-Nle, and Fmoc-Cys(Acm). This modification of the Example 1 procedure is applicable to the synthesis of other cPND peptides where an N-terminal Ac-Cys(Acm) is desirable.

EXAMPLE 9

Deprotection of cPND10 to Yield ₑPND9

The Acm protected Ac-Cys(Acm) may be converted to the free Ac-Cys-SH (free sulfhydryl) form of the peptide according to the procedure described in Atherton, E. et al., Chem. Soc. Perkin Trans., I, 2057 (1985). This procedure is applicable to removal of Acm thiol protection of peptides in preparation for conjugation with a thiophilic agent, such as bromoacetylated or maleimidated proteins or polysaccharides. A portion of cPND10 was dissolved in 10% aqueous acetic acid and treated with mercuric trifluoroacetate (10-fold excess). The pH was readjusted to 4 and the solution was stirred at room temperature while cleavage of the S-Acm groups was monitored by reverse-phase HPLC. When the reaction was judged completem, the solution was saturated with hydrogen sulfid gas. The mercury(II) sulfid precipitate was removed by centrufugation, and cPND9 was purified by RP-HPLC. The structure and purity of cPND9 was confirmed by FAB-MS, analytical HPLC, and amino acid analysis.

EXAMPLES 7–26 cPND Peptides Synthesized According to the Methods of Examples 6–9 and 19–20

The procedures established above in Examples 6–9 and below in Examples 25–26 for the synthesis of cPND7, cPND8, cPND9, cPND10, cPND31, and cPND32 respectively were applied, without any substantial modification, aside from changes in the peptide primary sequence and inclusion of appropriate protecting groups, in the synthesis of the cyclic form of synthetic PND peptides from many different isolates. Thus, all of the following peptides, synthesized according to these methods, may be N-terminal deprotected as necessary, and conjugated through -r- to form the conjugates of this invention:

| EX. * | NAME | STRUCTURE | FAB MB M⁺H |
|---|---|---|---|
| 7) | cPND8 | H—Nle—KHIGPGRAF, (ε) N——C=O, H | 1077 |
| 8) | cPND10 | Ac—Cys(Acm)—Nle—KHIGPGRAF, (ε) N——C=O, H | 1293 |
| 9) | cPND9 | Ac—Cys—Nle—KHIGPGRAF, (ε) N——C=O, H | 1223 |
| 10) | cPND11 | Z—Nle—KIGPGRAF, (ε) N——C=O, H | 1074 |
| 11) | cPND12 | H—Nle—KGPGRAF, (ε) N——C=O, H | 827 |
| 12) | cPND13 | Z—Nle—KGPGRAF, (ε) N——C=O, H | 961 |
| 13) | cPND14 | Z—Nle—kHIGPGRAF, (ε) N——C=O, H | 1211 |
| 14) | cPND15 | H—Nle—KQRGPGRAF, (ε) N——C=O, H | 1111 |
| 15) | cPND16 | Z—Nle—KSerIGPGRAF, (ε) N——C=O, H | 1161 |
| 16) | cPND21 | H—Nle—KRGPGRAF, (ε) N——C=O, H | 983 |
| 17) | cPND23 | Z—Nle—KHIGPGRA, (ε) N——C=O, H | 1063 |
| 18) | cPND24 | Z—Nle—KQRGPGRA, (ε) N——C=O, H | 1098 |
| 19) | cPND25 | H—Nle—KIGPGRA, (ε) N——C=O, H | |

-continued

| EX. * | NAME | STRUCTURE | FAB MB M+ H |
|---|---|---|---|
| 20) | cPND26 | Z—Nle—KGPGRA, (ε) N—C=O, H | 814 |
| 21) | cPND27 | H—Nle—KHIGPGRAF, (ε) N————C=O, H | 1077 |
| 22) | cPND28 | Z—Nle—KQRGPGRAF, (ε) N————C=O, H | 1245 |
| 23) | cPND29 | Z—Nle—KHIGPGRAFv, (ε) N————C=O, H | 1310 |
| 24) | cPND30 | Z—Nle—KHIGPGRVF, (ε) N————C=O, H | 1257 |
| 25) | cPND31 | H—Nle—N~KHIGPGRAF, (ε) (α) N—C(CH$_2$)$_2$CHNC=O, H OH$_2$NOC H | 1204 |
| 26) | cPND32 | H—Nle—N~KQRGPGRAF, (ε) (α) N—C(CH$_2$)$_2$CHNC=O, H OH$_2$NOC H | 1238 |

EXAMPLE 25

Synthesis of cPND31

Two grams (0.6 meq/gram) of Fmoc-Phe-Wang resin was loaded on an ABI 431A synthesizer. Fmoc single coupling protocols were used to add Fmoc-Ala, Fmoc-Arg(Tos), Fmoc-Pro, Fmoc-Ile, Fmoc-His(Trt), Boc-Lys(Fmoc), and Cbz-Nle to produce 3.7 grams of linear peptide resin having the sequence:
Boc-Lys(Ne-Z-Nle)-His(Trt)-Ile-Gly-pro-Gly-Arg(Tos)-Ala-Phe.

The peptide was cleaved from the resin by treating with 95% TFA, 5% water for two hours. The resin was removed by filtration, the TFA removed from the filtrate by evaporation in vacuo, and the residue was triturated with diethyl ether. The precipitate was recovered by filtration and drying to yield 1.7 grams of linear peptide having the sequence: H-Lys(N$^ε$-Z-Nle)-His-Ile-Gly-Pro-Gly-Arg(Tos)-Ala-Phe.

The peptide was treated with Boc-isoglutamine-ONp (0.71 grams, 2 nmoles,) and DIEA (0.35 ml, 2 mmoles) in DMF (10 ml) overnight at room temperature. The DMF was evaporated, and the residue treated with diethyl ether. The precipitate was recovered by filtration and washed with ethyl acetate. The dried peptide (1.9 grams) was treated with TFA (100 ml) for 0.5 hours. The TFA was evaporated in vacuo, the residue triturated with diethyl ether and the precipitate was recovered by filtration and dried.

The peptide was desalted on Sephadex G-10 in 10% aqueous acetic acid as the eluent. Peptide fractions were lyophilized to yield 1.2 grams (0.79 mmoles) of:
H-isoGln-LYs(N$^ε$-Z-Nle)-His-Ile-Gly-Pro-Gly-Arg(Tos)-Ala-Phe Two batches (0.55 gm, 0.36 mmoles) of the peptide were separately dissolved in 1000 mL ice cold DMF and DIEA (0.16 mL, 0.9 mmoles) and DPPA (0.12 mL were added and the solutions were stirred overnight at room temperature. The DMF was evaporated in vacuo and the residues combined and solubilized in CHCl$_3$. The organic fraction was washed with 5% aqueous citric acid, then dried over MgSo$_4$ and evaporated to yield 0.78 gm of crude cyclic peptide. This material was treated with liquid HF (10 mL) containing anisole (1 mL) for two hours at 0° C. The HF was evaporated and the residue was purified by graidien elution on reversed phase HPLC (Vydac C-18, 0–50% CH$_3$CN, over 50 minutes using 0.1% aqueous TFA as the buffer) to give 250 mg of pure cPND31 (M+H=1204).

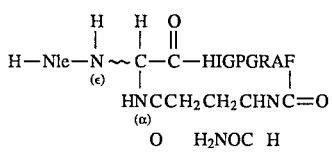

EXAMPLE 26

Synthesis of cPND32

Essentially the same procedure used in Example 25 for synthesis of cPND 31 was employed here except that the linear peptide that was cyclized had the sequence: H-isoGln-Lys($N^\epsilon$-Z-Nle)-Gln-Arg(Tos)-Gly-Pro-Gly-Arg-(Tos)-Ala-Phe, to generate cPND32 having the structure:

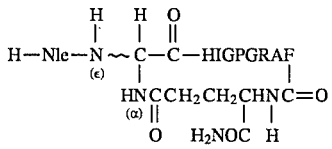

EXAMPLE 27

Preparation of Maleimidoethane Phosphonic Acid, (MEPA)

Ethoxy carbonyl maleimide, 169 mg, was added to 2-aminoethyl phosphonic acid, 125 mg, and sodium carbonate, 106 mg, in 1 ml of water at 0° C. The mixture was stirred for 20 minutes, then 4 ml of water was added and the mixture was stirred at room temperature for 1 hr. The solution was acidified to pH 5.5 with dilute sulfuric acid and concentrated in vacuo to 1 ml. The product was isolated by chromatography on three 1000µ reverse-phase TLC plates developed in water. Four bands were noted on examination of the developed plates under U.V. light. The third band at 15–16.7 cm from the origin was isolated; 100 mg of maleimidoethane phosphonic acid-sodium salt was recovered as an amorphous powder. The 200 MHZ NMR spectrum in $D_2O$ showed the maleimide hydrogens as a singlet at 7,2 ppm and the ethylene hydrogens as multiplets at 4.0 and 2.2 ppm.

EXAMPLE 28

Preparation of Maleimidoethane Sulfonic Acid, (MESA)

Using the reaction conditions of Example 27 but substituting 123 mg, taurine, in place of the 2-aminoethane phosphonic acid, the sodium salt of maleimidoethanesulfonic acid is recovered by TLC and lyophilization, as an amorphous powder.

EXAMPLE 29

Preparation of Maleimido-Succinic and Maleimido-Glutaric Acid

Substituting 133 mg, aspartic acid, or 157 mg glutamic acid, for aminonethane phosphonic acid in Example 27 gives the sodium salts of maleimido-succinic and 2-maleimido glutaric acid respectively.

B. Examples of Intermediate Activation and Coconjugate Formation

EXAMPLE 30

Preparation of OMPC-SH 10 mililiters of OMPC (3.2 mg/ml) was centrifuged, at 43,000 ram, 4° C. for 2 hours. The OMPC pellet was resuspended in 8 ml of thiolating solution (prepared by mixing 85 mg EDTA, 17 mg DTT, and 46 mg N-acetyl homocysteine thiolactone in 10 ml of pH 11 borate buffer). The thiolation reaction was allowed to proceed at room temperature overnight, and the solution was then centrifuged at 43,000 rpm, 4° C. for 2 hours. The OMPC-SH was resuspended in 10 ml of 0.01M, pH 8 phosphate buffer, recentrifuged, and resuspended in 9.3 ml of 0.01M, pH 8 phosphate buffer. An Ellman assay indicated a sulfhydryl titer of 0.496 µmoles/ml.

EXAMPLE 31

Preparation of MaleimidoPropionyl-cPND15

10 milligrams of cPND15 trifluoroacetate salt was dissolved in 0.3 ml of a 1:2 mixture of $H_2O$:MeCN. The solution was cooled in an ice bath and then 100 µL of 0.345M $NaHCO_3$ solution, followed by 3.5 mg of maleimidopropionic acid N-hydroxysuccinimide ester, was added. The reaction was allowed to proceed with stirring for one hour, followed by quenching with 3 µL of trifluroacetic acid. The reaction mixture was filtered through a 0.2 micron filter, and the filter was washed with 0.2 ml of water. The combined filtrates were injected onto a 2.15×25 cm Vydac C18 reverse phase column. The column was eluted isocratically for 10 minutes at a flow rate of 10 ml/min. with 25% MeCN/0.1% TFA, followed by gradient elution from 25 to 40% MeCN/0.1% TFA, over 20 minutes. The product eluting between 20 and 32 min was concentrated and lyophilized, yielding 7 mg of the trifluoroacetate salt of maleimidopropionyl-cPND15 as a white amorphous powder. FAB-MS revealed a major ion (M+H) at 1262. Titration for maleimide by Ellman assay quenching gave a concentration of 0.54 µmoles per mg of the maleimidopropionyl-cPND15.

EXAMPLE 32

Preparation of Maleimidopropionyl-cPND31

Following the procedure of Example 31, 37.6 mg of the trifluoroacetate salt of cPND31 was reacted with 8.3 mg of maleimidopropionyl N-hydroxysuccinimide ester in 0.4 ml of a 0.322M $NaHCO_3$ solution and 1.2 ml of 1:2 $H_2O$:MeCN, followed by quenching with 10.5 µl of TFA. Preparative HPLC (30% MeCN/0.1% TFA isocratic for 10 minutes followed by gradient elution from 30–50% MeCN over 5 min gave a product peak eluting between 18–25 min. The lyophilized product weighed 26 mg, and the maleimide titer was 0.57 µM/mg. FAB-MS gave a major ion (M+H) at 1356. Amino acid analysis gave Nle=460, β-alanine=420 and Lys=460 nmoles/mg. NMR analysis gave a singlet at 6.93 ppm (maleimide H).

EXAMPLE 33

Preparation of Maleimidopropionyl-CPND8

Following the procedure of Example 31, 3.5 mg of cPND8 trifluoroacetate salt was reacted with 1.5 mg of maleimidopropionyl (N-Hydroxy) succinimide in 0.24 ml of a 1:2 mg $H_2O$:MeCN solution, to which 0.12 ml of a 0.175M $NaHCO_3$ solution was added. 2.6 mg of maleimidopropionyl-cPND8 was recovered and subjected to preparative HPLC (30% MeCN/0.1% TFA isocratic for 10 minutes followed by gradient elution from 30–50% MeCN over 10 minutes). The peak eluting between 22.5–30 minutes was collected, concentrated and lyophilized. FAB-MS: M+H at 1228, M+Na at 1250. NMR ($D_2O$) maleimide hydrogen at 6.85 ppm.

EXAMPLE 34

Preparation of Maleimidopropionyl-CPND32

Following the procedure of example 5, ten milligrams of cPND32 trifluoroacetate salt are dissolved in 0.3 ml of a 1:2 mixture of $H_2O$:MeCN, 0.1 ml of a 0.35M $NaHCO_3$ solution. 3.2 mg of maleimidopropionyloxysuccinimide are added to give the maleimidopropionyl-cPND32 trifluoroacetate salt. The peptide is isolated by preparative HPLC using gradient elution from 25 to 40% MeCN in 0.1% TFA.

EXAMPLE 35

Conjugation of OMPC-SH with maleimidopropionyl-cPND15 and Maleimido Propionic Acid (MPA)

OMPC (10 ml of a 3.2 mg/ml solution) was thiolated according to Example 30, giving a solution containing 0.496 µM SH per ml. In a separate tube a solution of approximately 4 mg of MPA in 3 ml of water was prepared and titrated. The maleimido content was found to be 8.38 µM/ml. The MPP-cPND15 (7 mg) from Example 31 was dissolved in 0.8 ml of water and titrated to give a maleimido content of 3.84 µM/ml.

172 µl (0.4 eq) of MPA solution was added to the OMPC-SH solution (7 ml) in a centrifuge tube, under a nitrogen atmosphere, with gentle swirling. The mixture was allowed to react at room temperature for 10 min., then 540 µl (0.6 eq.) of maleimidopropionyl-cPND15 solution was added. The mixture was stoppered, allowed to stand for one hour, and then centrifuged (1000 RPM for 1 min.). The supernatant was dialyzed (12,000–14,000 m. wt. cut-off) against 4 L pH 7.5, 0.01M phosphate buffer. The dialysis was continued for an additional 8 hours with fresh buffer. The mixture was transferred to a stoppered vial and stored in the refrigerator. Lowry protein assay indicated the presence of 2.82 mg coconjugate protein per ml, and amino acid analysis showed the presence of 271 nmoles norleucine/ml. Using a molecular weight of 1.111 mg per nanomole, the peptide loading was calculated to be 10.7%. The overall yield (i.e. protein recovery) was about 80%. The excess MPP-cPND15 solution not used in the reaction was recovered by lyophilization.

EXAMPLE 36

Preparation of Maleimidobutyryl-cPND31, (MBP-CPND31)

Following the procedure of Example 31, 10.6 milligrams of cPND31 trifluoroacetate salt was dissolved in a solution composed of 0.45 ml 1:2 water:MeCN, and 0.15 ml of 0.25M $NaHCO_3$. γ-Maleimidobutyric acid N-hydroxysuccinimide ester (4.3 mg) was added and the mixture was stirred at 0° C. for one hour. The reaction was quenched with 3 µl of trifluoroacetic acid, and the peptide was isolated by preparative HPLC: 30% MeCN/1% TFA isocratic elution for 10 minutes, followed by a gradient from 30–50% MeCN over 10 minutes. A peak at 21.2 to 25 minutes was collected, concentrated and lyophilized to give 3.8 mg of white powder. FAB-MS revealed a M+H of 369.

EXAMPLE 37

Conjugation of OMPC-SH with Maleimidopropionyl-cPND31 and Maleimidopropionic Acid; Determination of Optimum MPA:Maleimidopropionic peptide (MPP) Ratio Decreasing fractional amounts of maleimidopropionic acid (MPA) were added to six tubes containing OMPC-SH (0.59 µM SH/ml) in pH 8, 0.1M phosphate buffer. After 10 minutes, excess maleimido propionyl-cPND31 was added to each tube to react with residual SH groups. After 1 hr. the tubes were centrifuged (1000 RPM, 1 min.) and the optical density of the supernatant in each tube determined at a wavelength of 275 nm. Dense precipitation was observed in tubes 4–6. The supernatant from tubes 1–3 were dialyzed against 4 liters of 0.01M pH 8 phosphate buffer, and the solutions were then analyzed:

| Tube # | 1 | 2 | 3 | 4 | 5 | 6 |
|---|---|---|---|---|---|---|
| % MPA | 67 | 50 | 33 | 25 | 17 | 10 |
| Absorbance (275 nm). | 4.05 | 3.9 | 6 | 0.4 | 0.11 | 05 |
| Lowry protein, (mg/ml) | 2.15 | 1.95 | 2.4 | ND[1] | ND | ND |
| AA assay (Nle)[2] | 63.6 | 78.6 | 157 | ND | ND | ND |
| Peptide loading[3] | 3.5% | 4.8% | 7.9% | ND | ND | ND |

1. ND = not determined
2. nmoles/ml
3. mg peptide (from Nle)/mg total protein

EXAMPLE 38

Conjugation of OMPC-SH with MPP-cPND31 and Maleimidophosphonic Acid (MEPA)

An aliquot of OMPC-SH suspension, prepared by the method of Example 30, (2 ml having 0.587 µM SH/ml) was charged to each of two centrifuge tubes. 103 µl (3.73 µM maleimide/ml, 0.33 eq) of MEPA was added to tube #1, and 78.6 µl (0.25 eq) was added to tube #2. After 15 minutes, the MPP-cPND31, 3.22 µM maleimide/ml was added to each tube (212 µl to #1 and 238 µl to #2). No precipitate was observed in either tube after one hour. After dialysis against 0.01M, pH 8 phosphate buffer, the solution was recovered from each tube, and analyzed:

| Tube | #1 | #2 |
|---|---|---|
| AU/275 | 7.5 | 8.2 |
| Lowry Protein, mg/ml | 2.34 | 2.52 |
| Nle, nM/ml | 183 | 250 |
| Peptide Loading, "j" | 9.4% | 12.3% |

EXAMPLE 39

Conjugation of OMPC-SH with MPP-cPND8 and Malemidopropionic Acid (MPA)

Following the procedure of Example 35, an aqueous solution of MPA (476 ul, 4.36 uM maleimide/ml, 0.4 eq) was added to a suspension of OPMC-SH (8.4 ml, 0.62 uM SH/ml) followed by MPP-cPND32 (560 uL, 5.58 uM maleimide/ml, 0.6 eq). After reaction according to Example 35, 9.0 ml of suspension was obtained having: AU/275 =6.9; Lowry protein=2mg/ml; Nle=275 nM/ml, Peptide loading= 14.89%.

EXAMPLE 40

Conjugation of OMPC-SH with MPP-cPND32and with MPA

To a suspension of OMPC-SH (9 ml, 600 µM SH/ml) prepared according to Example 30 is added a solution of MPA (392 ul, 5.5 µM maleimide/ml, 0.4 eq). After 10 minutes a solution of MPP-cPND32(704, µl, 4.6 µm maleimide/ml, 0.6eq) is added and the mixture allowed to react for one hour at room temperature. The reaction is then centrifuged (1000 RPM, 1 min) and the supernatant dialized against 4 l pH 7.5, 0.1M phosphate buffer. The post-dialysis suspension containing the coconjugate is recovered and stored at 4° C.

EXAMPLE 41

Conjugation of OMPC-SH with MBP-cPND31 and MPA

Following the procedure example 35 an aqueous solution of MPA (0.4 eq) is added to a suspension of OMPC-SH followed by a solution of maleimidobutyryl cPND31(0.6 eq). The product is purified by dialysis vs pH 8, 0.01M phosphate buffer and recovered as a suspension.

EXAMPLE 42

Preparation of Maleimidopropionyl-OMPC (MP-OMPC)

10 ml of OMPC(3.2 ng/nl) is centrifuged at 43,000 RPM, at 4° C. for 2 hours and the pellet is resuspended in 8 ml of a cooled solution of 1.6 mg sodium bicarbonate in 1:1 $H_2O$:MeCN. Maleimidopropionyl N-Hydroxy succinimide (2.6 mg) is added and the mixture is agitated for 1 hour on ice. 2 ml of 0.1M pH 6 phosphate buffer is added and the mixture is centrifuged at 43,000 RPM and 4° C. for 2 hours. The maleimidated OMPC is resuspended in 0.01M pH 7 buffer, recentrifuged and resuspended in pH 8 0.1M phosphate buffer. The maleimido content is determined by reaction of an aliquot with a known quantity of a N-acetylcysteine followed by Ellman assay.

EXAMPLE 43

Reaction of Maleimidopropionyl-OMPC with Thiolacetic Acid (TAA) and cPND9—SH

To a suspension of maleimidopropionyl-OMPC prepared by the method of Example 42 (8 ml, 0.6 uM maleimide/ml) is added an aqueous solution of TAA (192 µl, 10 µmolesSH/ml, 0.4 eq) with vigorous agitation. After 10 minutes cPND9 (720 ul, 0.4 uM SH/ml, 0.6 eq) is added and the mixture allowed to stand at room temperature for one hour. The mixture is centrifuged (1000 RPM, 1 min) and the supernatant is dialyzed for 18 hours vs. 4 L of pH 7.5, 0.01M phosphate buffer. The dialysis is continued for an additional 8 hours with fresh buffer and the dialysis suspension is recovered and stored at 4° C. Amino acid, and Lowry protein analyses allowing quantitation of peptide loading.

EXAMPLE 44

Preparation of Thiolated Succinoyl OMPC 10 ml of OMPC (3.2 mg/ml) is centrifuged at 43,000 RPM and 4° C. for 2 hours and the OMPC pellet is resuspended in 6.3 ml of pH 11 borate buffer. Two milliliters of the OMPC suspension are added to each of three tubes which are cooled in ice. An aliquot of succinic anhydride (0.1M in acetonitrile) is added to each tube with vigorous stirring. Succinic anhydride solution is added to tube #1 (8 µl), tube #2 (16 µl), and tube #3 (32 µl). The reactions are allowed to proceed for 2 hours at 0° C., and one hour at room temperature, followed by an addition to each tube of 2 ml of thiolating solution (prepared by mixing 85 mg EDTA, 17 mg DTT and 46 mg N-acetyl homocysteine thiolactone in 10 ml pH 11 borate buffer). The thiolation reactions are allowed to proceed at room temperature overnight and then each tube is centrifuged at 43,000 RPM, 4° C. for 2 hours. The thiolated succinoyl OMPC from each tube is resuspended in 10 ml of pH 8, 0.01 phosphate buffer, recentrifuged and resuspended in 2 ml of pH 8 0.01M phosphate buffer. The sulfhydryl titer in each tube is determined by Ellman assay.

EXAMPLE 45

Conjugation of Thiolated Succinoyl OMPC with MPP-cPND31

Each tube of thiolated, resuspended succinoyl OMPC from Example 20 is treated with an equivalent of a solution of maleimidopropionyl-cPND31. The reactions are allowed to proceed for one hour and the tubes are then centrifuged at 1000 RPM for 1 minute. The supernatants are dialyzed against 1 L of pH 8, 0.01M phosphate buffer. The conjugates are recovered and analyzed for norleucine and protein content.

EXAMPLE 46

Protocol for Inoculation of Animals with the Maleimidopropionyl-cPND31- or Maleimidopropionyl-cPND33- OMPC-Maleimidopropionic Acid Coconjugate of this Invention Alum was used as an adjuvant during the inoculation series. The inoculum was prepared by dissolving the coconjugate in physiologic saline at a final conjugate concentration of 300 µg/ml. Preformed alum (aluminum hydroxide gel) was added to the solution to a final level of 500 µg/ml aluminum. The conjugate was allowed to adsorb onto the alum gel for two hours at room temperature. Following adsorption, the gel with the conjugate was washed twice with physiologic saline and resuspended in saline to a protein concentration of 300 µg/ml.

African green monkeys were individually inoculated with three 300 µg doses or three 100 µg doses of the conjugate either adsorbed onto alum, or formulated with the Ribi adjuvant. Each dose was injected intramuscularly. The doses were delivered one month apart (week 0, 4 and 8). The animals were bled at intervals of two weeks. Serum samples were prepared from each bleed to assay for the development of specific antibodies as described in the subsequent examples.

EXAMPLE 47

Analysis of Sera for Anti-Peptide IgG Antibodies

Each serum sample is analyzed by enzyme-linked immunoadsorbent assay (ELISA). Polystyrene microtiter plates were coated with 0.5 µg per well of the synthetic peptide (not conjugated to OMPC) in phosphate-buffered physiological saline (PBS) at 4° C. Each well was then washed with PBS containing 0.05% TWEEN-20 (PBS-T). Test serum, diluted serially in PBS-T, was added to the peptide-containing wells and allowed to react with the adsorbed peptide for one hour at 36° C. After washing with PBS-T, alkaline phosphatase-conjugated goat anti-human IgG was added to the test wells and was allowed to react for one hour at 36° C. The wells were then washed extensively in PBS-T. Each well received 0.1% p-nitrophenyl phosphate in 10% diethanolamine, pH 9.8, containing 0.5 mM $MgCl_2 \bullet 6H_2O$. The ensuing reaction was allowed to proceed at room temperature for 30 minutes, at which time it was terminated by the addition of 3.0N NaOH.

The greater the interaction of antibodies in the test serum with the peptide substrate, the greater is the amount of alkaline phosphatase bound onto the well. The phosphatase enzyme mediates the breakdown of p-nitrophenyl phosphate into a molecular substance which absorbs light at a wavelength of 405 nm. Hence, there exists a direct relationship between the absorbance at 405 nm of light at the end of the ELISA reaction and the amount of peptide-bound antibody.

All the monkeys inoculated with the maleimidopropionyl-cPND31-OMPC-maleimidopropionic acid or the maleimidopropionyl-cPND33-OMPC-maleimidopropionic acid coconjugate developed antibodies specifically capable of binding the peptide.

EXAMPLE 48

Analysis of Sera for Activity which Specifically Neutralizes HIV Infectivity

Virus-neutralizing activity is determined with an assay described by Robertson et al., J. Virol. Methods 20:195–202 (1988). The assay measures specific HIV-neutralizing activity in test serum. The assay is based on the observation that MT-4 cells, a human T-lymphoid cell line, are readily susceptible to infection with HIV and, after a period of virus replication, are killed as a result of the infection.

The test serum is treated at 56° C. for 60 minutes prior to the assay. This treatment is required to eliminate non-specific inhibitors of HIV replication. Heat treated serum, serially diluted in RPMI-1640 cell culture medium, is mixed with a standard infection dose of HIV. The dose is determined prior to the assay as containing the smallest quantity of virus required to kill all the MT-4 cells in the assay culture after a period of 7–8 days. The serum-virus mixture is allowed to interact for one hour at 37° C. It then is added to $1.0 \times 10^5$ MT-4 cells suspended in RPMI-1640 growth medium supplemented with 10% fetal bovine serum. The cultures are incubated at 37° C. in a 5% $CO_2$ atmosphere for 7 days.

At the end of the incubation period, a metabolic dye, DTT, is added to each culture. This dye is yellow in color upon visual inspection. In the presence of live cells, the dye is metabolically processed to a molecular species which yields a blue visual color. Neutralized HIV cannot replicate in the target MT-4 cells and therefore does not kill the cells. Hence, positive neutralization is assessed by the development of blue color following addition of the metabolic dye.

All monkeys immunized with the maleimidopropionyl-cPND33-OMPC-maleimidopropionic acid coconjugate developed specific antibodies capable of neutralizing human immunodeficiency virus as described above.

EXAMPLE 49

Conjugation of OMPC with cPND33
1. Preparation of 3-Maleimidopropionic Acid Anhydride 3-Maleimidopropionic acid (226 mg) was covered with 5 mL of acetic anhydride and the mixture was heated at 130° C. for 3.75 hour, and then aged over night at room temperature. The solution was concentrated to an oil and the NMR spectrum ($CDCl_3$) indicated a mixture of the homoanhydride and the mixed anhydride of acetic and maleimidopropionic acids. The starting acid shows the methylen adjacent to the carbonyl as a triplet centered at 2.68 ppm whereas in the anhydride these resonances appear at 2.81 ppm. Purification was effected by fractional sublimation, first at 70° C. and 0.2 mm and then at 120° C. and 0.2 mm. The latter fraction was removed from the sublimer by dissolving in $CDCl_3$, affording 34 mg of pure homanhydride on evaporation of the solvent. This was recrystallized from $CDCl_3$ and cyclohexane affording material melting at 143°–147° C.

2. Selective Acylation of cPND33 cPND33 (22.5 mg, at estimated 70% peptide is equivalent to 15.75 mg or 5.212 micromoles) was dissolved in 12.0 mL of a 0.1M pH 5.25 morpholinoethane sulfonic acid buffer and cooled in an ice bath. Analysis of this solution and progress of the reaction was followed by HPLC on a 25 cm ODS column using 25% aqueous acetonitrile: 0.1% trifluoroacetic acid (TFA) as eluent. Maleimidopropionic acid anhydride (2.0 mg, 6.25 micromoles) was dissolved in 0.600 mL of dry tetrahydrofuran, and 0.5 mL of this solution (corresponding to 5.2 micromoles of anhydride) was added to the above peptide solution. After 30 sec., a 7 microliter aliquot was removed and evaluated by HPLC. This assay was repeated at 0.25, 0.50, 1.25, 2.25 and 3.0 hr. After 3.5 hr the solution was lyophilized. The lyophilizate was dissolved in 2.0 mL of 20% aqueous acetonitrile, filtered through a 0.2 micron filter and preparatively chromatographed in three 0.700 mL runs on a 21.2 mm×25 cm Zorbax C-18 column. The following elution program was used: flow rate=10 mL/min; isocratic elution with 25% aqueous acetonitrile/0.1% TFA (12 min); gradient to 28% acetonitrile (10 min); gradient to 35% acetonitrile (8 min). The tail fractions were isolated by concentration and lyophilization to afford 8.9 mg of recovered starting material (penultimate fraction) and 9.6 mg of a product which had a mass spectrum (FAB) indicating a molecular weight of 3172 (i.e the mono-maleimidopropionyl derivative of cPND33).

The product was further characterized by a sequence analysis looking for the absence of lysine (the absence of any sequence would imply terminal amino acylation). The results indicate that most but not all of the maleimidopropionyl moiety is bonded to the lysine closet to the carboxy terminus.

3. Co-Conjugation of Maleimidated cPND33 with Thiolated OPMC

A. Small Scale Experiment

An aqueous 3-maleimidopropionic acid (MPA) solution (1 mg/mL) was prepared. This was titred as follows: to 2.98 mL of a solution of N-acetylcysteine (0.2 micromoles/mL in pH 8.0 $PO_4$ buffer) was added 0.02 mL of the maleimidopropionic acid solution. After ageing for 10 minutes, 0.100 mL of Ellman reagent was added. The O.D. was determined at 412 nm using this material in the reference beam and a "blank" (prepared by substituting water for the sample) in the sample beam. A titer of 5.0 micromoles/mL of 3-maleimidopropionic acid was found by this Ellman "extinction" assay. The maleimidated peptide (MPP) from above (9.6 mg/0.800 mL of water) was titred in the same way and found to have 2.7 micromoles/mL.

OPMC thiolated with N-acetylhomocysteine thiolactone was found by Ellman Assay to have a titer of 0.775 micromoles SH/mL. To 0.5 mL of this thiolated OPMC solution in a ReactiVial was added 0.044 mL of the MPA solution and after ageing for 10 minutes at room temperature, 0.044 mL of the MPP solution was added. No precipitation of conjugate was noted.

B. Large Scale Experiment

To 8.5 mL (6.6 micromoles of SH) of the above thiolated OPMC solution was added 0.85 mL of the MPA solution (4.25 micromoles or 65% of MPA) and after ageing for 10 minutes 0.85 mL of the MPP solution (2.3 micromoles or 35% MPP) was added. The solution was aged at 4° C. for 16 hours after which time a precipitate was noticed. The precipitate was resuspended by a adjusting the pH to 8.13 with 0.005 mL of 5N NaOH. After ageing for 3 hours, a small amount of precipitate was removed by a low speed centrifugation. The conjugate was then purified by ultracentrifugation twice at 43K rpm, 4° C. for 2 hours. The pellets were resuspended with a Dounce homogenizer in 0.03M, pH phosphate buffer.

The final conjugate solution was assayed for protein (fd: 0.92 mg/mL) and amino acid analysis (Nle=60.35 nanomoles/mL, i.e. peptide; 139.6 nanomoles of beta alanine, =total maleimido compounds in conjugate). This corresponds to a 20.4% loading of the peptide by weight onto the protein.

The conjugate is a mixture consisting of cPND33 bonded to OMPC through the amino terminal norleucine, or one of the three internal lysines. The conjugate was tested in rabbits and found to be efficacious in raising HIV neutralizing antibodies.

While the foregoing specification teaches the principles of the present invention, with examples provided for the purpose of illustration, it will be understood that the practice of the invention encompasses all the usual variations, adaptations, modifications, or deletions as come within the scope of the following claims and its equivalents.

What is claimed is:

1. A coconjugate comprising the Outer Membrane Protein Complex (OMPC) of *Neisseria meningitidis b* and a Principal Neutralizing Determinant (PND) of Human immunodeficiency Virus (HIV) having the structure:

$_j$(PEP—A—)—OMPC—(—B—$a^-$)$_x$ wherein j is the peptide loading and is between 1% and 50% of the total coconjugate protein;

—A— consists essentially of the linkage:

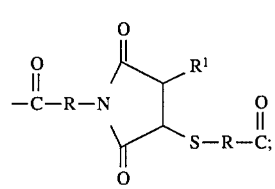

—B— consists essentially of the linkage:

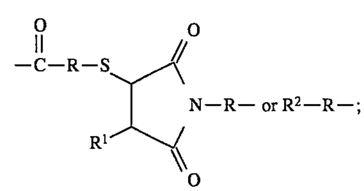

—$a^-$ is a low molecular weight moiety having an anionic or polyanionic character at physiological pH, and is from one to five residues of the anionic form of the carboxylic, sulfonic, or phosphonic acid;

X is the number of moles of B—$a^-$ in the coconjugate and is between 1% and 90% of m;

m is the molar amount of reactive nucleophilic functionalities in the OMPC prior to conjugation;

S is sulfur;

R is lower alkyl, substituted lower alkyl, cycloalkyl, substituted cycloalkyl, or phenyl;

$R^1$ is hydrogen, lower alkyl or —$SO_3H$;

$R^2$ is lower alkyl, carbonyl or lower acyl amino;

PEP is one or more PND peptides selected from the group consisting of:

| NAME | STRUCTURE |
|---|---|
| cPND1 | r-Nle—C—H—I—G—P—G—R—A—F—C—OH; (disulfide via xylyl linker) |
| cPND2 | r-Nle—C—I—G—P—G—R—A—F—C—OH; (disulfide via xylyl linker) |
| cPND3 | r-Nle—C—R—I—Q—R—G—P—G—R—A—F—V—T—C—OH; (disulfide via xylyl linker) |
| cPND4 | r-Nle—C—H—I—G—P—G—R—A—F—C—COOH; CH$_2$—S——S—CH$_2$ |
| cPND8 | r-Nle—K—H—I—G—P—G—R—A—F; (ε)N—H ——— C=O |
| cPND9 | r-Ac—Cys—Nle—K—H—I—G—P—G—R—A—F; (ε)N—H ——— C=O |
| cPND11 | r-Nle—K—I—G—P—G—R—A—F; (ε)N—H ——— C=O |
| cPND12 | r-Nle—K—G—P—G—R—A—F; (ε)N—H ——— C=O |
| cPND13 | r-Nle—K—G—P—G—R—A—F; (ε)N—H ——— C=O |
| cPND14 | r-Nle—K—H—I—G—P—G—R—A—F; (ε)N—H ——— C=O |
| cPND15 | r-Nle—K—Q—R—G—P—G—R—A—F; (ε)N—H ——— C=O |
| cPND16 | r-Nle—K—Ser—I—G—P—G—R—A—F; (ε)N—H ——— C=O |
| cPND21 | r-Nle—K—R—G—P—G—R—A—F; (ε)N—H ——— C=O |
| cPND23 | r-Nle—K—H—I—G—P—G—R—A; (ε)N—H ——— C=O |
| cPND24 | r-Nle—K—Q—R—G—P—G—R—A; (ε)N—H ——— C=O |
| cPND25 | r-Nle—K—I—G—P—G—R—A; (ε)N—H ——— C=O |
| cPND26 | r-Nle—K—G—P—G—R—A; (ε)N—H ——— C=O |
| cPND27 | r-Nle—K—H—I—G—P—G—R—A—F; (ε)N—H ——— C=O |
| cPND28 | r-Nle—K—Q—R—G—P—G—R—A—F; (ε)N—H ——— C=O |
| cPND29 | r-Nle—K—H—I—G—P—G—R—A—F—V; (ε)N—H ——— C=O |
| cPND30 | r-Nle—K—H—I—G—P—G—R—V—F; (ε)N—H ——— C=O |
| cPND31 | r-Nle—N(H)—K—H—I—G—P—G—R—A—F; (ε) N—C(CH$_2$)$_2$—CH—N—C=O; H  O  H$_2$NOC  H |
| cPND32 | r-Nle—N(H)—K—Q—R—G—P—G—R—A—F; (ε) N—C(CH$_2$)$_2$—CH—N—C=O; H  O  H$_2$NOC  H |
| PND142 | r-Y—N—K—R—K—R—I—H—I—G—P—G—R—A—F—Y—T—T—K—N—I—I—G—T; |
| PND-SC | r-N—N—T—T—R—Ser—I—H—I—G—P—G— |

R—A—F—Y—A—T—G—D—I—I—G—D—I;

PND135
r-N—N—T—R—K—Ser-I—R—I—Q—R—G—

P—G—R—A—F—V—T—I—G—K—I—G—N;

PND135-18
r-R—I—Q—R—G—P—G—R—A—F—V—T—I—

G—K—I—G—N;

PND135-12
r-R—I—Q—R—G—P—G—R—A—F—V—T;
PND-MN8
r-H—I—G—P—G—R—A—F;
PND-MN6
r-G—P—G—R—A—F;
PND-LAV-1
r-I—Q—R—G—P—G—R—A—F;
PND-SF2
r-I—Y—I—G—P—G—R—A—F;
PND-NY5
r-I—A—I—G—P—G—R—T—L;
PND-CDC4
r-V—T—L—G—P—G—R—V—W;

PND-RF
r-I—T—K—G—P—G—R—V—I;
PND-ELI
r-T—P—I—G—L—G—Q—Ser-L;
PND-Z6
r-T—P—I—G—L—G—Q—A—L;
PND-MAL
r-I—H—F—G—P—G—Q—A—L;
PND-Z3
r-I—R—I—G—P—G—K—V—F; and cPND33    H—Nle Cys Tyr Asn Lys Arg Lys Arg
(SEQ.ID.NO:1)      |         Ile His Ile Gly Pro Gly
          CH₂      Arg Ala Phe Tyr Thr
           |       Thr Lys Asn Ile
           |       Ile Gly Cys—OH
           |                    |
           S ——————— S—CH₂;

r is the position of the linkage between the peptide and the OMPC, with the proviso that cPND33 may be linked through the amino terminal Nle or one of the internal Lys residues.

2. A coconjugate having the structure:

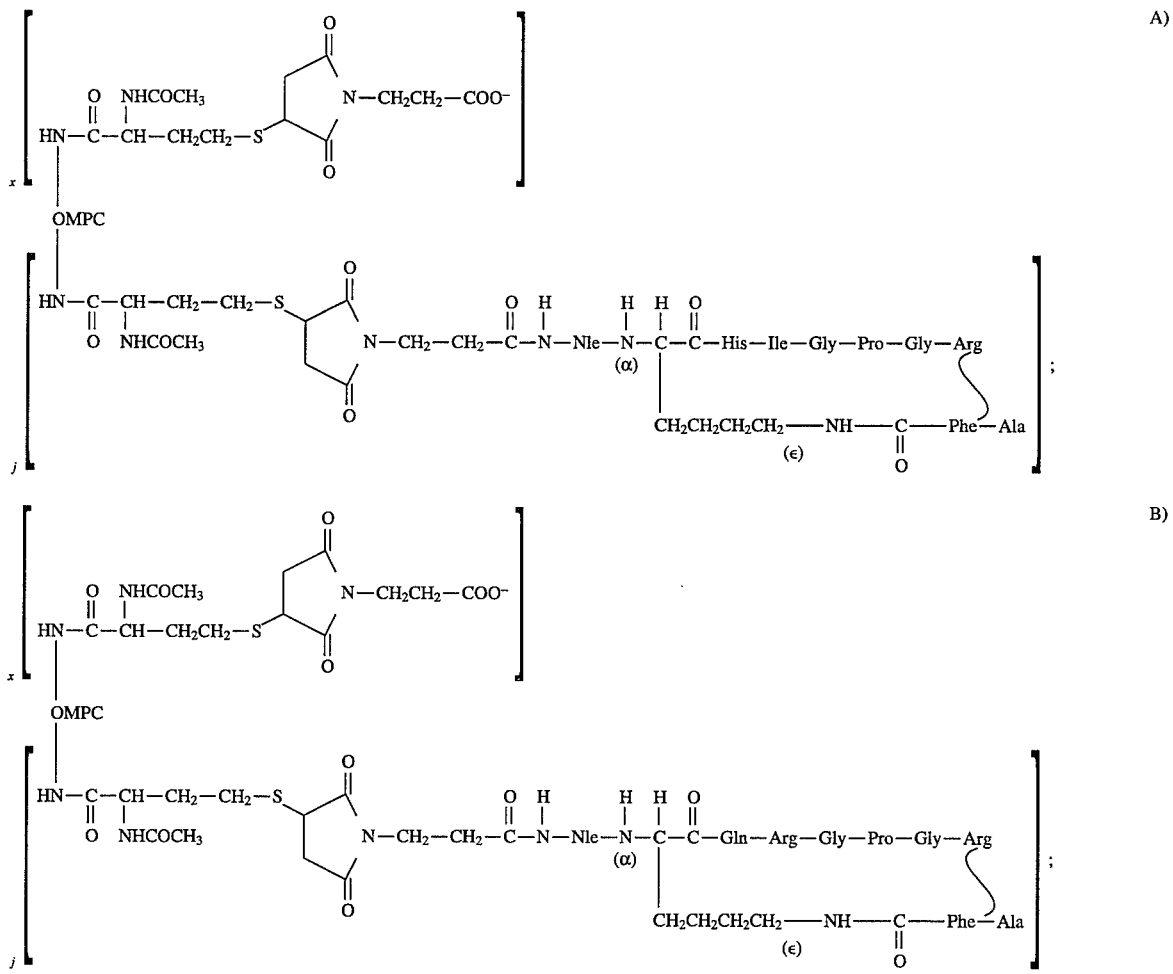

-continued
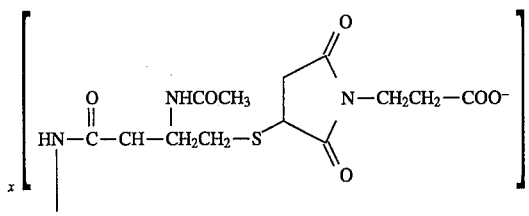
C)
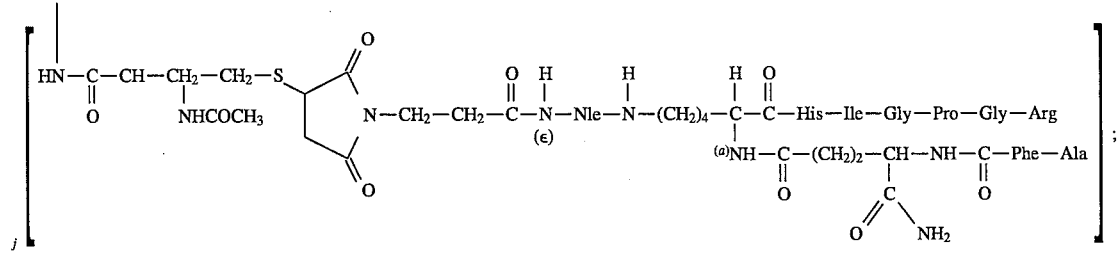
;
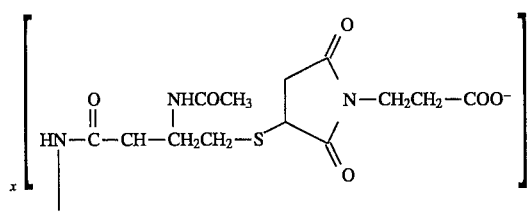
D)
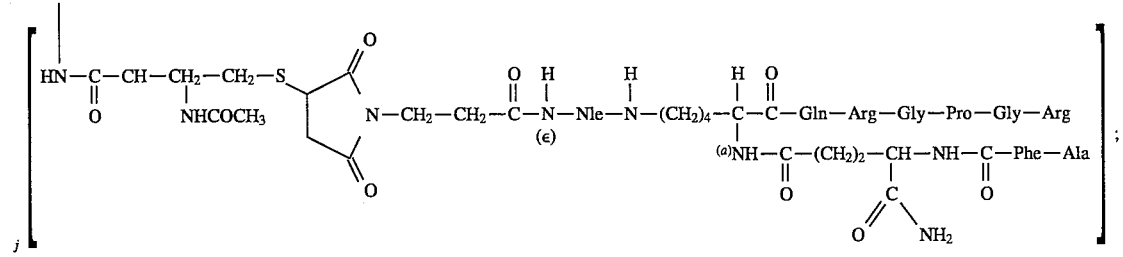
;
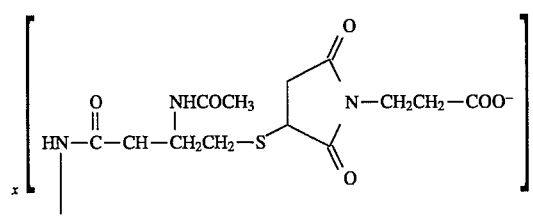
E-1)
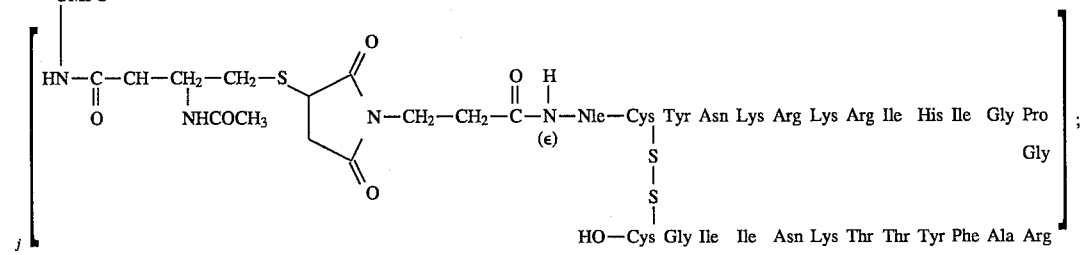
;

-continued
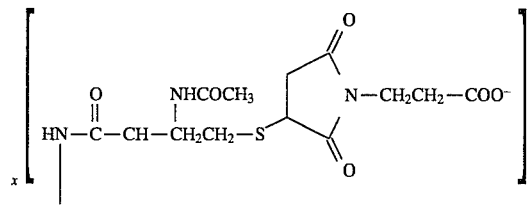
E-2)
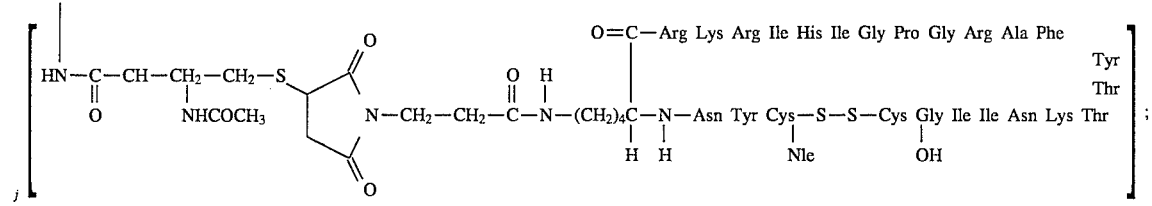
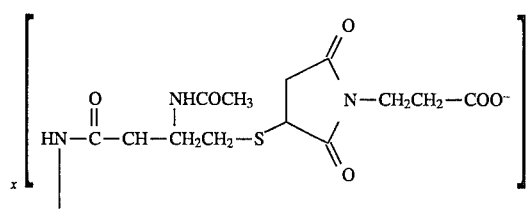
E-3)
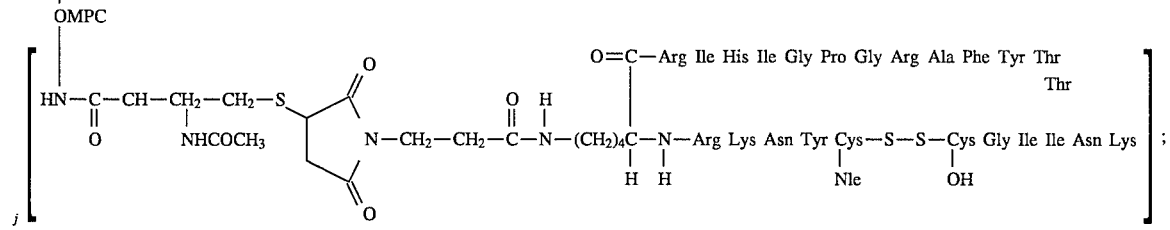
and
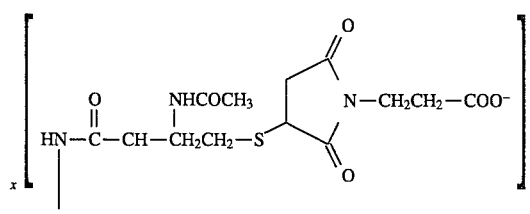
E-4)
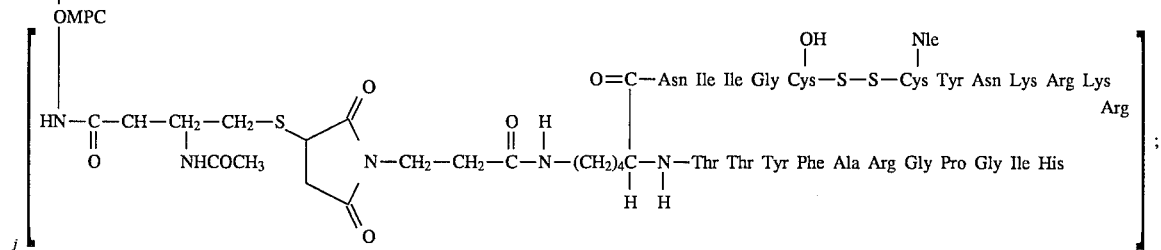
or a pharmaceutically acceptable salt thereof, wherein
OMPC is the outer membrane protein complex of *Neisseria meningitidis b;*
x is between 10% and 50% of the molar amount of reactive nucleophilic functionalities in OMPC prior to conjugation;
j is between 1% and 50% of the total protein mass of the coconjugate; and
S is sulphur.
* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 26 amino acids
( B ) TYPE: amino acid
( D ) TOPOLOGY: both ( i i ) MOLECULE TYPE: peptide ( i x ) FEATURE:
( A ) NAME/KEY: Modified-site
( B ) LOCATION: 1
( D ) OTHER INFORMATION: /label=Nle
/ note= "norleucine"

( i x ) FEATURE:
( A ) NAME/KEY: Disulfide-bond
( B ) LOCATION: 2..26

( x i ) SEQUENCE DESCRIPTION: SEQ ID NO:1:

| | | | | | | | | | | | | | | | |
|---|---|---|---|---|---|---|---|---|---|---|---|---|---|---|---|
| Leu | Cys | Tyr | Asn | Lys | Arg | Lys | Arg | Ile | His | Ile | Gly | Pro | Gly | Arg | Ala |
| 1 | | | | 5 | | | | | 10 | | | | | 15 | |
| Phe | Tyr | Thr | Thr | Lys | Asn | Ile | Ile | Gly | Cys | | | | | | |
| | | | 20 | | | | | 25 | | | | | | | |